United States Patent
Wagner et al.

(10) Patent No.: US 10,947,347 B2
(45) Date of Patent: Mar. 16, 2021

(54) HYROPHILIC ETHYLENE OXIDE FREE EMULSIFIER COMPRISING DENDRIMERIC POLYHYDROXYLATED ESTER MOIETIES

(71) Applicant: Momentive Performance Materials GmbH, Leverkusen (DE)

(72) Inventors: Roland Wagner, Bonn (DE); Sebastian Maass, Elsdorf (DE); Narayan Mukherjee, Sleepy Hollow, NY (US); Karl-Heinz Sockel, Leverkusen (DE); Katharina Streicher, Leverkusen (DE)

(73) Assignee: Momentive Performance Materials GMBH, Leverkusen (DE)

( * ) Notice: Subject to any disclaimer, the term of this patent is extended or adjusted under 35 U.S.C. 154(b) by 396 days.

(21) Appl. No.: 14/512,071

(22) Filed: Oct. 10, 2014

(65) Prior Publication Data

US 2016/0102179 A1   Apr. 14, 2016

(51) Int. Cl.

| | | |
|---|---|---|
| *C08G 77/38* | (2006.01) | |
| *C08L 83/06* | (2006.01) | |
| *A61K 8/892* | (2006.01) | |
| *A61K 8/894* | (2006.01) | |
| *A61K 8/06* | (2006.01) | |
| *A61K 8/891* | (2006.01) | |
| *A61Q 1/00* | (2006.01) | |
| *A61Q 5/00* | (2006.01) | |
| *A61Q 5/06* | (2006.01) | |
| *A61Q 5/08* | (2006.01) | |
| *A61Q 17/04* | (2006.01) | |
| *A61Q 19/00* | (2006.01) | |
| *A61Q 19/02* | (2006.01) | |
| *C08G 77/14* | (2006.01) | |
| *C08G 77/16* | (2006.01) | |
| *A61Q 17/02* | (2006.01) | |
| *A61Q 1/02* | (2006.01) | |
| *A61Q 1/10* | (2006.01) | |
| *A61Q 15/00* | (2006.01) | |
| *A61Q 19/04* | (2006.01) | |

(52) U.S. Cl.
CPC .............. *C08G 77/38* (2013.01); *A61K 8/064* (2013.01); *A61K 8/891* (2013.01); *A61K 8/892* (2013.01); *A61K 8/894* (2013.01); *A61Q 1/00* (2013.01); *A61Q 5/00* (2013.01); *A61Q 5/06* (2013.01); *A61Q 5/065* (2013.01); *A61Q 5/08* (2013.01); *A61Q 17/04* (2013.01); *A61Q 19/00* (2013.01); *A61Q 19/02* (2013.01); *C08L 83/06* (2013.01); *A61K 2800/544* (2013.01); *A61Q 1/02* (2013.01); *A61Q 1/10* (2013.01); *A61Q 15/00* (2013.01); *A61Q 17/02* (2013.01); *A61Q 19/04* (2013.01); *C08G 77/14* (2013.01); *C08G 77/16* (2013.01)

(58) Field of Classification Search
CPC ........ A61K 8/064; A61K 8/891; A61K 8/892; A61K 8/894; A61K 2800/544; A61Q 1/00; A61Q 1/02; A61Q 1/10; A61Q 5/00; A61Q 5/06; A61Q 5/065; A61Q 5/08; A61Q 15/00; A61Q 17/02; A61Q 17/04; A61Q 19/00; A61Q 19/02; A61Q 19/04; C08G 77/14; C08G 77/16; C08G 77/38; C08L 83/06

See application file for complete search history.

(56) References Cited

U.S. PATENT DOCUMENTS

| | | | |
|---|---|---|---|
| 4,698,178 | A | 10/1987 | Huttinger et al. |
| 5,104,647 | A | 4/1992 | Policello |
| 5,136,063 | A | 8/1992 | O'Lenick, Jr. |
| 5,180,843 | A | 1/1993 | O'Lenick, Jr. |
| 5,210,133 | A | 5/1993 | O'Lenick, Jr. |
| 5,226,923 | A | 7/1993 | O'Lenick, Jr. |
| 5,248,783 | A | 9/1993 | O'Lenick |
| 5,411,729 | A | 5/1995 | O'Lenick, Jr. |
| 5,446,183 | A | 8/1995 | O'Lenick, Jr. |
| 5,446,184 | A | 8/1995 | O'Lenick, Jr. |
| 5,475,125 | A | 12/1995 | O'Lenick, Jr. |
| 5,558,806 | A | 9/1996 | Policello et al. |
| 5,674,832 | A | 10/1997 | Keys |
| 6,090,758 | A | 7/2000 | Pillon et al. |
| 6,221,811 | B1 | 4/2001 | Policello et al. |
| 6,388,042 | B1 | 5/2002 | O'Lenick, Jr. |
| 6,727,340 | B1 | 4/2004 | O'Lenick, Jr. |

(Continued)

FOREIGN PATENT DOCUMENTS

| | | |
|---|---|---|
| EP | 0 091 257 A2 | 10/1983 |
| EP | 1 683 852 A1 | 7/2006 |

(Continued)

OTHER PUBLICATIONS

B. Grüning et al., "Neuartige Emulsionen mit siliziumorganischen Copolymeren als Emulgatoren", Special Surfactants, Tenside Surf. Det. 29; pp. 78-83 (1992) 2.

(Continued)

*Primary Examiner* — Trevor Love

(74) *Attorney, Agent, or Firm* — Joseph S. Ostroff

(57) ABSTRACT

There is provided herein an organofunctional polysiloxanes comprising hydroxyl polyester groups made by reaction of epoxy functional polyorganosiloxanes and oligmeric polyesters based on polyhydroxy carboxylic acids.

There is also provided methods for making the organofunctional polysiloxanes and agricultural, coating, personal care and home care applications containing the organofunctional polysiloxanes.

19 Claims, No Drawings

(56) References Cited

U.S. PATENT DOCUMENTS

| | | |
|---|---|---|
| 6,891,051 B1 | 5/2005 | Wohlman et al. |
| 7,083,800 B1 | 8/2006 | Terren et al. |
| 7,199,095 B2 | 4/2007 | Lentsch et al. |
| 7,399,734 B2 | 7/2008 | Grabowski et al. |
| 7,655,744 B2 | 2/2010 | Miyanaga |
| 2003/0096919 A1 | 5/2003 | Ichinohe |
| 2004/0009131 A1 | 1/2004 | Simonnet et al. |
| 2004/0071741 A1 | 4/2004 | Derian |
| 2005/0008592 A1 | 1/2005 | Gardel et al. |
| 2005/0084467 A1 | 4/2005 | Miyanaga |
| 2005/0261133 A1 | 11/2005 | Nakanishi et al. |
| 2006/0013793 A1 | 1/2006 | Themens |
| 2007/0129492 A1* | 6/2007 | Colborn ............ B64C 1/1492 525/100 |
| 2008/0167390 A1 | 7/2008 | Archer et al. |
| 2012/0289649 A1* | 11/2012 | Wagner ............. A61K 8/893 524/588 |
| 2013/0216801 A1* | 8/2013 | Kadoki ............. C08G 64/06 428/215 |

FOREIGN PATENT DOCUMENTS

| | | |
|---|---|---|
| EP | 1 816 154 A1 | 8/2007 |
| EP | 2 030 605 A1 | 3/2009 |
| EP | 2 223 989 A1 | 9/2010 |
| EP | 2 243799 A1 | 10/2010 |
| JP | 2005-082925 | 4/1993 |
| JP | 2005-089494 | 4/1993 |
| WO | 2007/075927 A1 | 7/2007 |
| WO | 2011/064255 A1 | 6/2011 |
| WO | 2011064255 | 6/2011 |

OTHER PUBLICATIONS

D. Schaefer, "Silicone Surfactants; Part II: Organomodified Polydimethyl Siloxanes as Surface Active Ingredients in Cosmetic Formulations", Special Surfactants, Tenside Surf. Det. 27; pp. 154-158 (1990) 3.

R. Wagner et al., "Silicon-Modified Cartohydrate Surfactants II: Siloxanyl Moieties Containing Branched Structures", Applied Organometallic Chemistry, vol. 10, pp. 437-450; (1996).

H.G. Hauthal et al., "A Report of: The 53rd SEPAWA Congress with 2nd European Detergents Conference 2006", SOFW—International Journal for Applied Sciences, vol. 132, Dec. 2006.

International Search Report and Witten Opinion of the International Searching Authority from PCT/US2015/053045 dated Oct. 11, 2015.

* cited by examiner

HYROPHILIC ETHYLENE OXIDE FREE EMULSIFIER COMPRISING DENDRIMERIC POLYHYDROXYLATED ESTER MOIETIES

The invention concerns dendrimer based hydrophilic and lipophilic modified polysiloxanes which preferably comprise ester units and which are preferably suitable as emulsifiers, in textile softeners, antifoams, foam stabilizers, demulsifiers, emulsion preventors and apiculture chemicals, in particular as O/W and W/O-emulsifiers for cosmetic uses.

BACKGROUND OF THE INVENTION

Siloxane based W/O-emulsifiers comprising ethylene oxide units are used extensively in liquid to paste-like cosmetic formulations such as e.g. creams and lotions. By using these emulsifiers it has become possible to emulsify large amounts of water in oil (high internal phase ratio emulsions). Such emulsions at a pleasant, light feeling on the skin.

It has been shown that oils differing strongly with regard to the molecular weight and the polarity, such as hydrocarbons, fatty acid esters and silicone oils can be emulsified so as to be stable long-term. This is due to the chemical structure of such siloxane based W/O-emulsifiers, which are made up of a siloxane backbone chain, hydrophilic polyethylene oxide units and hydrophobic long chain alkyl groups. The hydrophilic polyether units mediate the connection to the water phase, the long chain alkyl groups bond the oil phase and the siloxane backbone chain stays in the phase boundary.

During the further development of this approach it was suggested to create emulsifiers by cohydrosilylation of SiH-containing siloxanes with allyl polyethers and undecenoic acid fatty alcohol esters or undecenoic acid fluoroalcohol esters respectively, which have good compatible and degradable fatty acid units as oil compatible components.

As an alternative, trials were undertaken to convert polyethylene oxide based siloxanes by esterification with fatty acids or esterification with dicarboxylic acids respectively in combination with alkoxylated fatty acids, alkoxylated fatty alcohols, glycerol fatty acids or neutralization of the carbon acid function with fatty amines into W/O-emulsifiers. A specific disadvantage of this product group is that hydrophilic and hydrophobic groups cannot orientate independently of one another.

A general disadvantage of all of these ethylene oxide units containing, siloxane based W/O-emulsifiers is that the proportion of polyethylene oxide units contained therein in combination with sunlight is made responsible for skin sensitisations.

Alkylene oxide free siloxane surfactants based on reducing, reduced or oxidized saccharides are known. Further, combinations of these hydrophilic mono- and disaccharide structures with hydrophobic moieties have been described in the literature. Disadvantage of saccharide based concepts is the limited availability of strongly hydrophilic, appropriately functionalized di- and oligosaccharides.

It is further well known to use glycerol modified siloxanes as a spreading additive. Polyglycerol modified siloxanes have become known as a component in formulations for the treatment of fibres. Branched polyglycerol modified siloxanes and modified siloxanes have been described in the literature.

For the prevention of the skin sensitization problems, siloxane-based W/O-emulsifiers have been presented, which are based on the cohydrosilylation of SiH-containing siloxanes with unsaturated oligoglycerols and long-chained alkenes. Disadvantages of oligoglycerol based concepts are the difficulties to control the molecular weight and especially the degree on functionalization which is a key element to react them with silicone precursors.

The etherification of the polyglycerol units positioned on the siloxane chain with e.g. lauryl alcohol results in emulsifiers, which are to be used in solid W/O-emulsions. Again, this solution is disadvantageous in that hydrophilic and hydrophobic groups cannot orientate independently of one another.

Dibenhates derived from allyl glycerol were added to α,ω-SiH siloxanes and resulted in waxes, which do not comprise emulsifying characteristics. This is also the case for those waxes, which are derived from allyl alcohol fatty acid esters.

Ethylene oxide-free siloxane-based W/O-emulsifiers comprising readily degradable hydrophobic tatty acid ester units as well as hydrophilic hydroxylated carboxylic acid ester units have been disclosed. These hydrophobic fatty acid units can be introduced independently from the hydrophilic hydroxylated carboxylic acid ester units. However, it is unclear how strongly hydrophilic O/W emulsifiers can be synthesized.

There is a need of strongly hydrophilic ethylene oxide-free siloxane-based O/W-emulsifiers which comprise strongly hydrophilic polyhydroxylated carboxylic acid ester units and optionally hydrophobic fatty acid ester units, wherein these strongly hydrophilic polyhydroxylated carboxylic acid polyester units can be introduced independently from the optional hydrophobic fatty acid units.

SUMMARY OF THE INVENTION

The object of the present application is to describe the synthesis of strongly hydrophilic polyethylene oxide-free siloxane-based O/W-emulsifiers which comprise readily degradable polyhydroxylated carboxylic acid polyester units as a hydrophilic component and optionally fatty acid units as an oil soluble component and wherein the addition of the hydrophilic and hydrophobic components can follow independently of one another. It is a further object of the application to describe the use of the polyethylene oxide-free siloxane-based O/W-emulsifiers in cosmetic formulations.

It was surprisingly found that polysiloxane compositions of the formula (1) defined below could solve the problems described above, particularly of the preparation of the emulsifiers, which substantially do not comprise polyalkylene oxide groups, and are able to emulsify with a high stability high amounts of a broad spectrum of oils in a water phase.

The polysiloxane compound of the present invention has the general formula (1):

$$[M_a D_b D^*_c T_d Q_e]_f \quad (I)$$

wherein
$M = R^1 R^2 R^3 SiO_{1/2}$;
$D = R^4 R^5 SiO_{2/2}$;
$D^* = R^6 R^7 SiO_{2/2}$;
$T = R^5 SiO_{3/2}$;
$Q = SiO_{4/2}$;
with
$a = 1-10$
$b = 0-1000$
$c = 0-1000$
$d = 0-1$
$e = 0-1$
$f = 1-10$ wherein $R^1$, $R^2$, $R^3$, $R^4$, $R^5$, $R^6$ and $R^8$ are each independently selected from the group consisting of monovalent hydrocarbon groups having from 1 to 8 carbon atoms, and an aryl or alkaryl hydrocarbon group of from 6 to 22 carbon atoms, or $R^7$;

$R^7$ is selected from the group consisting of $R^9$, $R^{10}$ and $R^{11}$, wherein $R^9$ is selected from the group consisting of —Z-(A-E$^1$)$_y$, —Z-E$^2$ and —Z—NH—C(O)—R$^{12}$, wherein Z is a bivalent or trivalent straight-chained, cyclic or branched, saturated or unsaturated $C_2$ to $C_{20}$ hydrocarbon residue which can comprise one or more groups selected from —O—, —NH—,

and can be substituted by one or more OH groups,

A is a bivalent residue selected from the group consisting of

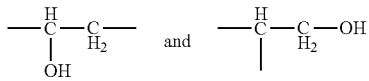

$E^1$ is selected from the group consisting of $E^2$ and $E^3$ wherein $E^2$=—O—C(O)—R$^{12}$, wherein $R^{12}$ is a dendrimer like branched hydrocarbon residue with up to 100 carbon atoms, which can comprise one or more groups selected, from —O—, —C(O)—, and is substituted by one or more OH groups,

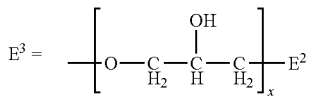

wherein $E^2$ is defined above, and x=1–4, y=1 or 2

$R^{10}$ is selected from the group consisting of —Z-(A-E$^4$)$_y$, —Z-E$^5$ and —Z—NH—C(O)—R$^{13}$, wherein Z and A are defined above, $E^4$ is selected from the group consisting of $E^5$ and $E^6$ wherein $E^5$=—O—C(O)—R$^{13}$, wherein $R^{13}$ is a straight-chained, cyclic or branched, saturated or unsaturated hydrocarbon residue kith up to 9 carbon atoms, which can comprise one or more groups selected from —O—, —NH—, —NR$^{14}$—, —C(O)—, and is substituted by one or more OH groups, wherein R$^{14}$ is a straight-chained, cyclic or branched, saturated or unsaturated hydrocarbon residue with up to 6 carbon atoms,

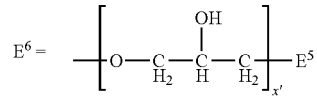

wherein $E^5$ is defined above, and x'=1–4, y' 1 or 2

$R^{11}$ is selected from the group consisting of —Z-(A-E$^7$)$_y$, —Z-E$^8$ and —Z—NH—C(O)—R$^{15}$, wherein Z and A are defined above, $E^7$ is selected from the group consisting of $E^8$ and $E^9$ wherein $E^8$=—O—C(O)—R$^{15}$, wherein $R^{15}$ is a straight-chained, cyclic or branched, saturated or unsaturated hydrocarbon residue with 10 to 50 carbon atoms, which can comprise one or more groups selected from —O—, —NH—, —NR$^{16}$—, —C(O)—,)-, and is optionally substituted by one or more OH groups, wherein $R^{16}$ is a straight-chained, cyclic or branched, saturated or unsaturated hydrocarbon residue with up to 6 carbon atoms,

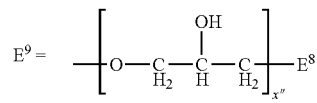

wherein $E^8$ is defined above, and x"=1–4, y"=1 or 2.

Accordingly, the polysiloxane compounds according to the invention substantially do not comprise polyalkylene oxide units, such as, in particular, polyethylene oxide and/or polypropylene oxide units with more than 4 repetitive units of alkylene oxides. Preferably the polysiloxane compounds according to the invention do not comprise polyalkylene oxide units.

In a preferred embodiment the polysiloxane compounds according to the invention comprise siloxy structural elements selected from the following structures:

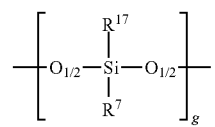

wherein $R^{17}$ is $C_1$ to $C_{22}$-alkyl, fluoro-substituted $C_1$ to $C_{22}$-alkyl or aryl, $R^{17}$ is preferably methyl, and g=0–600,

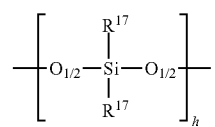

wherein the groups $R^{17}$ can be the same or different and are selected from $C_1$ to $C_{22}$-alkyl, fluoro-substituted $C_1$ to $C_{22}$-alkyl and aryl, $R^{17}$ is preferably methyl, and
h=0–700, preferably 3 to 500, more preferably 5 to 200, even more preferably 10 to 100,

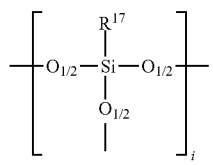

wherein $R^{17}$ is as defined above, $R^{17}$ is preferably methyl, and
i=0–10, preferably 0,

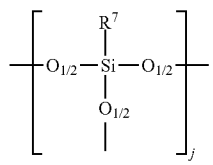

wherein $R^7$ is as defined above, and
j=0–10, preferably 0,

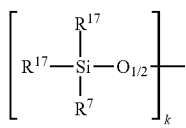

wherein $R^7$ and $R^{17}$ are as defined above, $R^{17}$ is preferably methyl, and k=0–30,

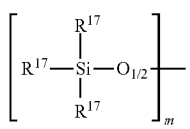

wherein $R^{17}$ is as defined above, $R^{17}$ is preferably methyl, and
m=0–30, preferably 1 to 6, more preferably 2,

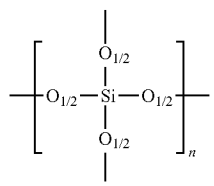

wherein n=0–10, preferably 0,
g+h+i±j±k+m+n=12–1000.

In a further preferred embodiment of the polysiloxane compounds according to the invention, the $R^9$ is mandatory group and $R^{10}$ and $R^{11}$ are optional groups, and they are linked via ester units —C(O)O— to the polymer. This means that the polysiloxane compounds according to the invention comprise in addition to the silicone typical substituent $R^{17}$ either exclusively hydrophilic dendrimer like substituent $R^9$ or
hydrophilic dendrimer like substituent $R^9$ in combination with other hydrophilic substituent $R^{10}$ or
hydrophilic dendrimer like substituent $R^9$ in combination with lipophilic substituent $R^9$ or
hydrophilic dendrimer like substituent $R^9$ in combination with other hydrophilic substituent $R^{10}$ and lipophilic substituent $R^{11}$.

In the context of the invention
the hydrophilic residues $R^9$ and $R^{10}$ have a log P (25° C.) of <0.5, and
the lipophilic residues $R^{11}$ have a log P (25° C.) of ≥0.5, wherein log P (25° C.) corresponds to the distribution coefficient of the corresponding compounds H—$R^{10}$ and H—$R^{11}$. According to the invention the corresponding distribution coefficients are determined for the sake of simplicity by means of the commercially available log P calculating software by the company ACD (ACD Inc., 133 Richmond St. W., Suite 605. Toronto, ON, Canada M5H 2L3 e.g. in Perspectives in Drug Discovery and Design, 19: 99-116, 2000), which are based on well-characterized log P contributions of single atoms structure fragments and intramolecular interaction between different fragments. Alternatively, the experimental determination in a water/n-octanol mixture (water: 50 ml, octanol: 50 ml, substance to be determined H—$R^{10}$ and H—$R^{11}$: 1 ml) at 25° C. is also possible.

In a further preferred embodiment the polysiloxane compounds according to the invention comprise structural elements selected from the following structures:

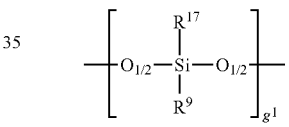

wherein $R^9$ and $R^{17}$ are defined above, $R^{17}$ is preferably methyl, and
$g^1$=0–300, preferably 2 to 200, more preferably 2 to 50, even more preferred 3 to 30,

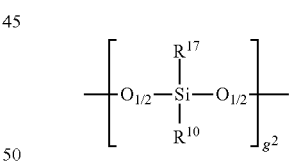

wherein $R^{10}$ and $R^{17}$ are defined above, $R^{17}$ is preferably methyl, and
$g^2$=0–300, preferably 0 to 200, more preferably 0 to 50, even more preferred 0 to 30, specifically 0 to 10,

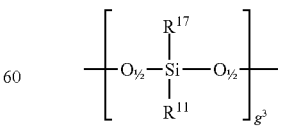

wherein $R^{11}$ and $R^{17}$ are defined above, $R^{17}$ is preferably methyl, and
$g^3$=0–300, preferably 0 to 200, more preferably 0 to 50, even more preferred 0 to 40, specifically 0 to 10,

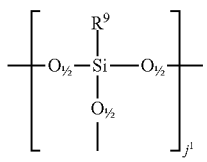

wherein $R^9$ is defined above, and
$j^1$=0–10, preferably 0,

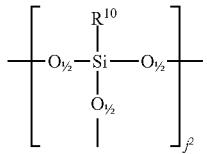

wherein $R^{10}$ is defined above, and
$j^2$=0–10, preferably 0,

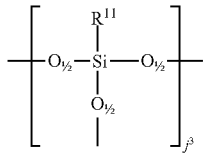

wherein $R^{11}$ is defined above, and
$j^3$=0–10, preferably 0,

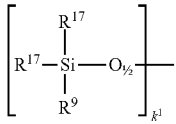

wherein $R^9$ and $R^{17}$ are defined above, $R^{17}$ is preferably methyl, and
$k^1$=0–15, preferably 0–2,

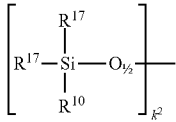

wherein $R^{10}$ and $R^{17}$ defined above, $R^{17}$ is preferably methyl, and
$k^2$=0–15, preferably 0–2,

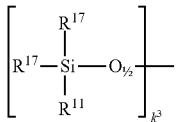

wherein $R^{11}$ and $R^{17}$ are defined above, $R^{17}$ is preferably methyl, and $k^3$=0–15, preferably 0–2, and
$g^1+g^2+g^3+h+i+j^1+j^2+j^3+k^1+k^2+k^3+m+n$=12 to 1000, preferably 15 to 400, more preferably 20 to 200, even more preferably 30 to 150.

In one specific expression of this embodiment of the invention the polysiloxane compounds consist of

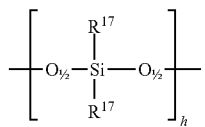

wherein the groups $R^{17}$ can be the same or different and are selected from $C_1$ to $C_{22}$-alkyl, fluoro-substituted $C_1$ to $C_{22}$-alkyl and aryl, preferably methyl, and
h=0–700, preferably 3 to 500, more preferably 5 to 200, even more preferably 10 to 100, and

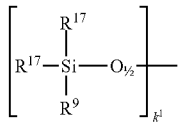

wherein $R^{17}$ is, as defined above, preferably methyl, and $R^9$ is as defined above, and
$k^1$=2, and
with
$h+k^1$ 2 to 1000, preferably 2 to 400, more preferably 2 to 200, even more preferably 2 to 100, most preferred 2 to 50, especially 2 to 30.

This means that in this very specific expression the substituents $R^9$ are exclusively located in the terminal groups of the polysiloxane compound.

In a preferred embodiment the molar ratio of the $R^9$ comprising siloxy units to the "non-modified", only $R^{17}$-comprising siloxy units is 10:1 to 1:10, more preferably 5:1 to 1:10, even more preferably from 2:1 to 1:10, specifically 2:1 to 1:5, even more specific 1:1 to 1:5.

In one preferred embodiment, hydrophilic residues $R^{10}$ and/or the lipophilic residues $R^{11}$ are not present in the polysiloxane compounds according to the invention.

If the ratio $R^9$ to $R^{17}$ is ≥0.2, the polysiloxane compounds according to the invention preferably can be used as compatibilizers for lipophilic phases, e.g., O/W emulsifiers yielding emulsions and microemulsions, i.e., for cosmetic formulations, defoamers, particularly preferred the use as demulsifiers in the oil and gas industry for faster and better separation of crude oil and water, as coagulants for rubber latex, as additive for anti-blocking mar resistance, as lubricant or lubricating additive, as tissue softeners or in tissue softener composition as self-emulsifying alklylene oxide-free softener or as shear stable emulsifier in textile treatment formulations, as foam stabilizers for aqueous foams indetergents, dishwashing liquids and in general-purpose cleaners, cosmetic fatty phases such as creams, as plastic and thermoplastic or elastomer additives for the hydrophilization and the improved wettability of thermoplastic or elastomeric surfaces.

If the ratio $R^9$ to $R^{17}$ is ≤0.2, the polysiloxane compounds according to the invention preferably can be used as W/O-emulsifiers, i.e. for cosmetic formulations, for example sun screen formulations, as foam stabilizers for polyurethane foams, demulsifiers in the oil and gas industry, or also as defoamers or in defoaming formulations, for example, diesel fuels or as coating additive for flow and levelling of paints coating compositions, as additive for anti-blocking, mar resistance, as lubricant or lubricating additive, as tissue softeners or in tissue softener compositions as self-emulsifying alkylene oxide-free softener or as shear stable emulsifier in textile treatment formulations.

In another preferred embodiment of the invention the molar ratio of the siloxy units comprising the dendrimer residue $R^9$ and the siloxy units comprising hydrophilic residues $R^{10}$ and lipophilic residues $R^9$ in the polysiloxane compounds according to the invention amounts to 1:0.01 to 1:100, more preferred 1:0.1 to 1:10, even more preferred 1:0.1 to 1:5, specifically 1:0.1 to 1:3, even more specific 1:0.1 to 1:1.

The incorporation of additional siloxy units comprising hydrophilic residues $R^{10}$ and/or lipophilic residues $R^{11}$ in the polysiloxane compounds according to the invention helps to further fine tune the emulsifier properties with respect to the specific applications. Directionally, additional hydrophilic residues $R^{10}$ help to adjust the O/W emulsifier properties of the polysiloxane compounds according to the invention. On the other side, additional lipophilic residues $R^{11}$ strengthen the susceptibility for oil phases and help to adjust the W/O emulsifier properties of the polysiloxane compounds according to the invention.

It is particularly preferred that the polysiloxane compounds according to the invention comprise siloxy units of the structures:

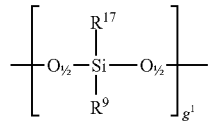

wherein $R^9$ and $R^{17}$ are defined above, $R^{17}$ is preferably methyl, and
$g^1$=1–300, preferably 2 to 200, more preferably 2 to 50, even more preferred 3 to 30,

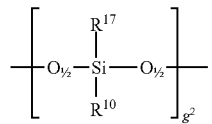

wherein $R^{10}$ and $R^{17}$ are defined above, $R^{17}$ is preferably methyl, and
$g^2$=0–300, preferably 0 to 200, more preferably 0 to 50, even more preferred 0 to 30, specifically 0 to 10,

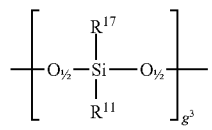

wherein $R^{11}$ and $R^{17}$ are defined above, $R^{17}$ is preferably methyl, and
$g^3$=0–300, preferably 0 to 200, more preferably 0 to 50, even more preferred 0 to 40, specifically 0 to 10,

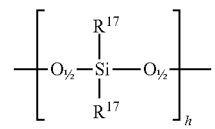

wherein the groups $R^{17}$ can be the same or different and are selected from $C_1$ to $C_{22}$-alkyl, fluoro substituted $C_1$ to $C_{22}$-alkyl and aryl, preferably methyl, and
h=0–700, preferably 3 to 500, more preferably 5 to 200, even more preferably 10 to 100, and

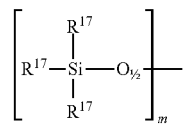

wherein $R^{17}$ is as defined above, $R^{17}$ is preferably methyl, and
m=0–30, preferably 1 to 6, more preferably 2.

Accordingly, preferred polysiloxane compounds according to the invention are linear trimethylsilyl end-stopped polysiloxane compounds.

In further preferred embodiments of the polysiloxane compounds according to the invention at least one, several or all of the following definitions are fulfilled in each case:

$R^{17}$ selected from $C_1$ to $C_{10}$-alkyl, which, if necessary, can be substituted with 1 to 13 fluoro atoms, and aryl, more specifically, $R^{17}$ is selected from $C_1$ to $C_6$-alkyl, which, if necessary, can be substituted with 1 to 13 fluoro atoms, phenyl;

Z is a bivalent or trivalent straight-chained, cyclic or branched, saturated or unsaturated $C_2$ to $C_{10}$-hydrocarbon residue, which can comprise —O— groups and can be substituted by one or more OH groups, more specifically, Z is a bivalent or trivalent straight-chained, cyclic or branched, saturated or unsaturated $C_2$ to $C_6$-hydrocarbon residue, which can comprise one or more —O— groups and can be substituted by one or more OH groups; and y=1.

In a preferred embodiment, $R^{12}$ is dendrimer like branched hydrocarbon residue with up to 70 carbon atoms, which can comprise one or more groups selected from —O—, —C(O)—, and is substituted by one or more OH groups. $R^{13}$ is a straight-chained, cyclic or branched, saturated or unsaturated hydrocarbon residue with up to 4 carbon atoms, which can comprise one or more groups selected from —O—, —NH—, —NR$^{13}$—, —C(O)—, and is substituted by one or more OH groups, wherein $R^{13}$ is a straight-chained cyclic or branched, saturated or unsaturated hydrocarbon residue with up to 6 carbon atoms, $R^{15}$ is a straight-chained, cyclic or branched, saturated or unsaturated hydrocarbon residue with 10 to 30 carbon atoms, which can comprise one or more groups selected from —O—, —NH—, —NR$^{13}$—, —C(O)—,)—, and is optionally substituted by one or more OH groups, wherein $R^{13}$ is a straight-chained, cyclic or branched, saturated or unsaturated hydrocarbon residue with up to 6 carbon atoms.

In another preferred embodiment, $R^{12}$ is

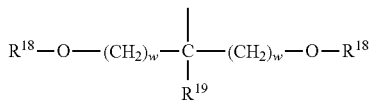

wherein
$R^{19}=R^{17}$ or H,
w=1–3,
$R^{18}=$H or

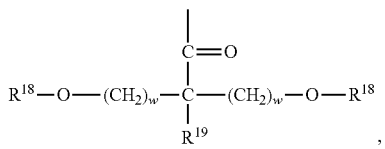

provided that the total number of carbon atoms in the dendrimer like residue $R^{12}$ is 5 to 70 and at least one ester bond is present in the residue structure.

In a further preferred embodiment $R^{19}$ is $CH_3$, and w=1, and the number of ester bonds present in the residue structure is 1 to 14, more preferred 1 to 10, even more preferred 1 to 7, specifically 1 to 5.

In further preferred embodiments of the polysiloxane compounds according to the invention, at least one, several or all of the following definitions are fulfilled in each case:

$Z=-CH_2CH_2CH_2-O-O-CH_2-$, $-CH_2CH_2CH_2CH_2-$, $-CH=CH_2CH_2-$, $-CH=CH_2CH_2CH_2-$,

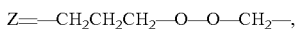

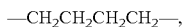

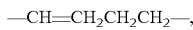

p=1 to 4,
(wherein * marks a bond in each case)
wherein the bond to the silicon takes places in the 2-position.
x=1.
Z-A- can also be selected from the cyclic structures which are derived from cyclic epoxides, such as

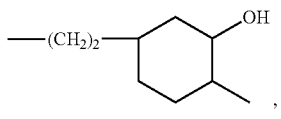

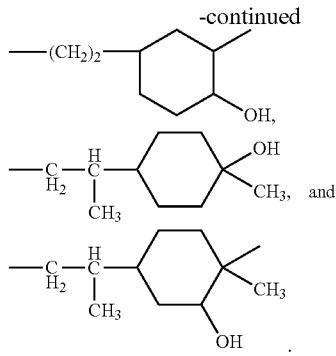

According to the invention, the polysiloxane compounds are preferably produced by the following processes which are characterized in that an epoxy functional polysiloxane is reacted with one or more than one monocarboxy functionalized dendrimer, optionally at the same time or subsequently with other hydrophilic and/or hydrophobic carboxylic acids or partially esterified carboxylic anhydrides and, if necessary, subsequently with primary or secondary amines.

More specifically the following preferred synthetic pathways are available:
a) an epoxy functional polysiloxane is reacted with one or more than one monocarboxy functionalized dendrimer,
b) an epoxy functional polysiloxane is reacted with one or more than one monocarboxy functionalized dendrimer, at the same time or subsequently with other hydrophilic and/or hydrophobic carboxylic acids or partially esterified carboxylic anhydrides,
c) an epoxy functional polysiloxane is reacted with one or more than one monocarboxy functionalized dendrimer, and subsequently with primary or secondary amines,
d) an epoxy functional polysiloxane is reacted with one or more than one monocarboxy functionalized dendrimer, at the same time or subsequently with other hydrophilic and/or hydrophobic carboxylic acids or partially esterified carboxylic anhydrides and subsequently with primary or secondary amines.

Alternatively, the monocarboxy functionalized dendrimers can be reacted first with unsaturated epoxides, like allyl glycidyl ether or vinyl cyclohexene yielding unsaturated esters of the dendrimers. In a subsequent step these unsaturated esters of the dendrimers can undergo hydrosilylation reactions with SiH functionalized silicone precursors yielding the target compounds.

It is within the scope of this synthetic protocol that the unsaturated esters of the dendrimers undergo a cohydrosilylation with SiH functionalized silicone precursors in the presence of other unsaturated functional compounds, i.e. allyl glycidyl ether, vinyl cyclohexene oxide, $C_8$ to $C_{20}$ fatty acid allyl esters, N,N-dimethylallylamine. The incorporation of these additional co-monomers either targets a compatibility optimization with organic compounds (i.e. $C_8$ to $C_{20}$ fatty acid allyl esters) or allows the incorporation of additional functional groups (i.e. via allyl glycidyl ether, vinyl cyclohexene oxide, N,N-dimethylallylamine) which tune the HLB value of the polysiloxane compound and/or charge the structure.

The application of the afore-mentioned concepts relating to
several hydrophilic and/or lipophilic acid and amino components various addition sequences leads to chemically differently composed component parts which finally go into the end product.

Starting points for the synthesis are in particular SiH-functional polysiloxanes, wherein hydrogen is formally replaced by substituents corresponding to $R^9$ and optionally $R^{10}$ and $R^{11}$.

Insofar as they are not commercially available, these SiH-functional polysiloxanes can be produced by known processes, e.g. by equilibration (Silicone, Chemie und Technologic, Vulkan-Verlag Essen 1989, p. 82-84), It is within the bounds of the invention to use several different SiH-functional polysiloxanes.

In one embodiment, epoxy groups are first introduced from the SiH-functional polysiloxanes, preferably by hydrosilylation reaction with olefinically or acetylenically unsaturated epoxy compounds.

Thus, preferred epoxy functional precursor structures are formed

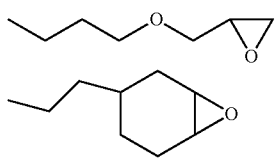

Alternatively, appropriate aminosiloxanes can be produced by known alkaline catalysed equilibrating reactions, which for example comprises —$CH_2CH_2CH_2NH_2$, —$CH_2CH_2CH_2NHCH_3$, —$CH_2CH_2CH_2NHCH_2CH_2NH_2$ substituents on the D-siloxane units (Silicone, Chemie und Technologic, Vulkan Verlag Essen 1989, p. 28-30). These reactively functionalised intermediary siloxane stages can be converted in a further step into the polysiloxane compounds according to the invention, for example by reaction with carboxylic acids under formation of amines, with epoxy functional compounds under formation of amino alcohols or with hydroxylated alcohols, also under formation of amino alcohols.

For introducing of the dendrimeric element $R^9$ preferably monocarboxy acid functionalized polyhydroxylated esters of the following structure are reacted with the epoxy functionalized silicones

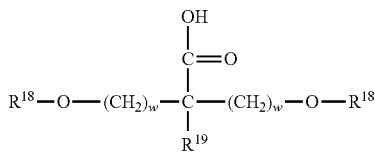

wherein $R^{18}$ and $R^{19}$ as defined above.

A preferred starting material for the synthesis these monocarboxy acid functionalized polyhydroxylated esters is 2,2-bis-(hydroxymethyl) propionic acid

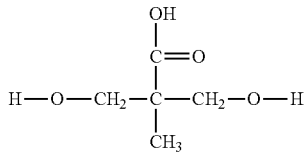

The formation of dendrimer like oligomers of this acid by intermolecular esterification of the neat acid is state of the art (Magnusson et. al., Macromolecules 2000, 33, 3099-3104). It is carried out in the presence of a strong acid, i.e. $H_2SO_4$ as catalyst at i.e. 140° C. Depending on the reaction conditions dimers, timers, tetramers and higher esterification condensates can be obtained. Typically, the reaction products represent mixtures of different oligomers.

It was found surprisingly, that monocarboxy acid functionalized polyhydroxylated acids. i.e. 2,2-bis-(hydroxymethyl) propionic acid, can be oligomerized in the presence of water and a strong acid as catalyst. The ratio monocarboxy acid functionalized polyhydroxylated acid:water determines the degree on oligomerization. The higher the ratio the higher the degree on oligomerization. A preferred ratio monocarboxy acid functionalized polyhydroxylated acid water is 99.9:0.1 to 40:60, more preferred 99:1 to 40:60, even more preferred 97:3 to 40:60, specifically 97:3 to 50:50, more specifically 95:5 to 50:50.

The reactions are carried out at 25 to 150° C., preferably at 50 to 150° C., more preferably at 90 to 150° C., even more preferably at 90 to 150° C., specifically at 90 to 140° C., more specifically at 100 to 140° C.

The catalyst concentration is in the range of 0.05 to 5%, preferably 0.1 to 5%, more preferably 0.5 to 5%, even more preferably 0.5 to 2%.

Strong acids are used as catalysts. Examples are mineral acids like $H_2SO_4$, strong organic acids, for example sulfonic acids like toluene sulfonic acid or strongly acidic ion exchange resins, for example, sulfonic acid functions containing resins like sulfonated polystyrene resins.

The reaction time ranges from 1 to 30 hours, preferably from 3 to 30 hours, even more preferably from 5 to 30 hours.

Typically, the reaction products represent mixtures of different oligomers. For the purpose of illustration a dimer of 2,2-bis-(hydroxymethyl) propionic acid

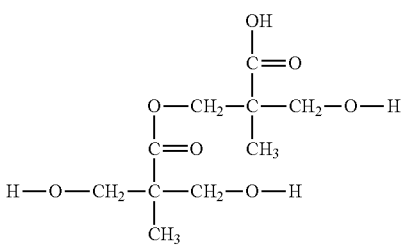

may also contain two possible trimers

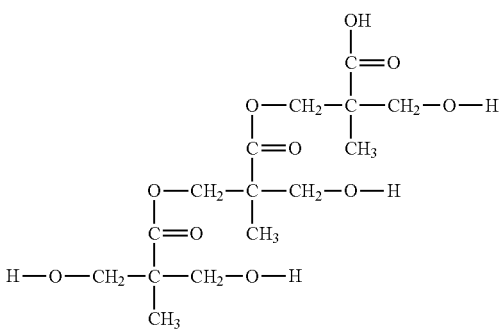

-continued and

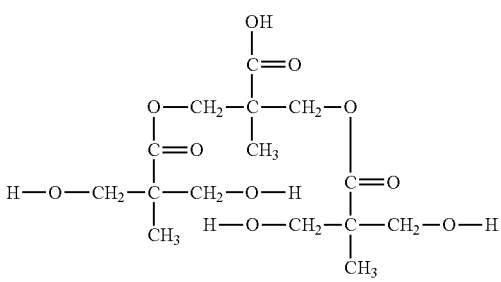

In another embodiment of the invention the monocarboxy acid functionalized polyhydroxylated acid, i.e. 2,2-bis-(hydroxymethyl) propionic acid, is reacted with unsaturated alcohol or epoxy precursors, i.e. hex-(1)-en-(6)-ol or allyl glycidyl ether, first. Afterwards, the oligomerization takes place in the presence or absence of water with a subsequent addition of the formed unsaturated polyhydroxylated ester derivatives to an SiH fluid.

In another embodiment of the invention the monocarboxy acid functionalized polyhydroxylated acid, i.e. 2,2-bis-(hydroxymethyl) propionic acid, is oligomerized in the presence or absence of water yielding the monocarboxy acid functionalized polyhydroxylated esters, and afterwards this is reacted with unsaturated alcohol or epoxy precursors, i.e. hex-(1)-en-(6)-ol or allyl glycidyl ether. Afterwards, the unsaturated polyhydroxylated ester derivatives are added to an SiH fluid.

In another embodiment of the invention the monocarboxy acid functionalized polyhydroxylated acid, i.e. 2,2-bis-(hydroxymethyl) propionic acid, is oligomerized in the presence of hydrophilic $C_2$ to $C_9$ carboxylic acids. Examples are glycolic acid, lactic acid, γ-hydroxy butyric acid, 2,3-dihydroxy propionic acid, α,β-dihydroxy butyric acid, α,γ-dihydroxy butyric acid, gluconic acid, succinic acid, maleic acid, phthalic acid, terephthalic acid, citric acid, benzene 1,3,4-tricarboxylic acid and 1,3,5-tricarboxylic acid. These oligomerizations are carried in the presence or absence of water. Copolyesters are obtained.

In another embodiment of the invention the monocarboxy acid functionalized polyhydroxylated acid, i.e. 2,2-bis-(hydroxymethyl) propionic acid, is oligomerized in the presence of $C_8$ to $C_{40}$ carboxylic acids. Examples are decanoic acid, undecenic acid, lauric acid, oleic acid, stearic acid, rhicinolic acid. These oligomerizations are carried in the presence or absence of water. It is within the scope of the invention to oligomerize the monocarboxy acid functionalized polyhydroxylated acid first and then to add the $C_8$ to $C_{40}$ acid for a final esterification step. It is also within the scope of the invention to oligomerize the monocarboxy acid functionalized polyhydroxylated and the $C_8$ to $C_{40}$ acid together in one step. Typically, the reaction products obtained according to this embodiment of the invention possess surfactant properties. They possess the structure

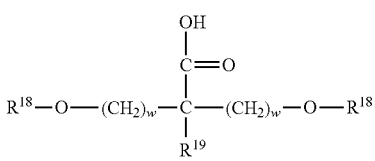

with at least one $R^{18}$ group comprising an ester moiety of the structure —OC(O)($C_7$-$C_{39}$ HYDROCARBON).

In another embodiment of the invention the monocarboxy acid functionalized polyhydroxylated acid, i.e. 2,2-bis-(hydroxymethyl) propionic acid, are reacted with $C_8$ to $C_{40}$ hydrocarbon based epoxides. Examples are octane-1-oxide, decene-1-oxide, dodecene-1-oxide, tetradecene-1-oxide, hexadecene-1-oxide, octadecene-1-oxide, octyl glycidyl ether, decyl glycidyl ether, dodecyl glycidyl ether, oleyl glycidyl ether and stearyl glycidyl ether. These reactions are carried out in the presence or absence of water. It is within the scope of the invention to react a fraction of the monocarboxy acid functionalized polyhydroxylated acid with the desired quantity of the epoxide first yielding ester or ether bonds and subsequently add the remaining portion of the monocarboxy acid functionalized polyhydroxylated acid. It is also within the scope of the invention to oligomerize the monocarboxy acid functionalized polyhydroxylated acid first and subsequently add the epoxide yielding ester or ether bonds. The reaction products obtained according to this embodiment of the invention possess surfactant properties.

The esterification yields structures

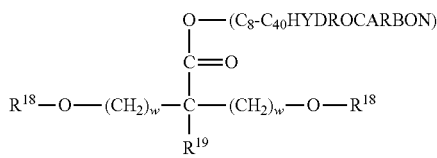

whereas the etherification yields

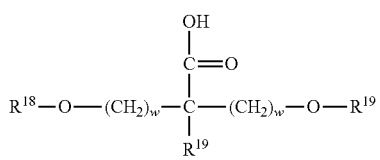

with at least one $R^{18}$ group comprising an ether moiety of the structure —O($C_8$-$C_{40}$ HYDROCARBON), In another embodiment of the invention the monocarboxy acid functionalized polyhydroxylated acid, i.e. 2,2-bis-(hydroxymethyl) propionic acid, are reacted with silane and carbosilane moieties containing epoxides. The silane and carbosilane moieties containing epoxides possess the structure

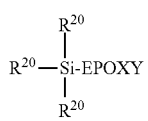

wherein
EPOXY=$C_3$ to $C_{20}$ moiety containing an epoxy function,
$R^{20}$=$R^{17}$ or a moiety of the formula

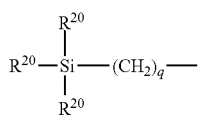

with q=1 to 3, preferably 1 to 2, more preferably 1, and a total number of Si atoms of 1 to 7, preferably 1 to 5, even more preferably 1 to 3, specifically 1 to 2.

These silane and carbosilane moieties containing epoxides can be synthesized from unsaturated epoxide precursors, for example, allyl glycidyl ether and vinyl cyclohexene oxide, and corresponding SiH functional silane and carbosilane precursors, Typical SiH functional silane and carbosilane precursors possess the structures

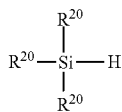

wherein
$R^{20}$=$R^{17}$ or a moiety of the formula

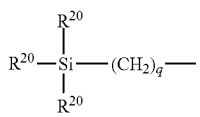

with
q=1 to 3, preferably 1 to 2, more preferably 1, and
and a total number of Si atoms of 1 to 7, preferably 1 to 5, even more preferably 1 to 3, specifically 1 to 2.

These reactions are carried out in the presence or absence of water. It is within the scope of the invention to react a fraction of the monocarboxy acid functionalized polyhydroxylated acid with the desired quantity of the epoxide first yielding ester or ether bonds and subsequently add the remaining portion of the monocarboxy acid functionalized polyhydroxylated acid. It is also within the scope of the invention to oligomerize the monocarboxy acid functionalized polyhydroxylated acid first and subsequently add the epoxide yielding ester or ether bonds. The reaction products obtained according to this embodiment of the invention possess surfactant properties.

The esterification yields silane or carbosilane structures

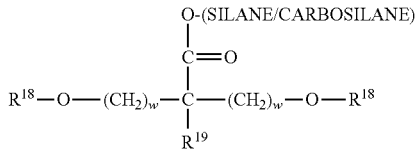

whereas the etherification yields

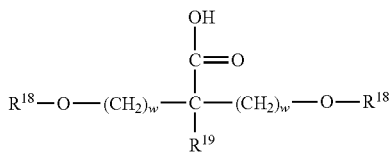

with at least one $R^{18}$ group comprising an ether moiety of the structure —O-(SILANE/CARBOSILANE).

For introducing the hydrophilic elements $R^{10}$, hydroxyl groups comprising carboxylic acids or at least one carboxylic acid group and at least one hydroxyl group comprising esters or lactones can be used.

The hydroxyl groups comprising carboxylic acids are monohydroxy and polyhydroxy carboxylic acids, for example glycolic acid, lactic acid, γ-hydroxy butyric acid, 2,3-dihydroxy propionic acid, 2,2-bis-(hydroxymethyl) propionic acid, α,β-dihydroxy butyric acid, α,γ-dihydroxy butyric acid, gluconic acid, glucopyranosylarabinoeic acid. The use of very long-chained hydroxy carboxylic acids, for example ricinoleic acid is possible, but less preferred.

For the introduction of the hydrophilic residues $R^9$ preferably mono or polycarboxylic functional carboxylic acids with <$C_{10}$ atoms or hydroxy functional carboxylic acids are used.

It is within the scope of the invention to use the acids for carrying out the reaction as an acid or also as an ester, particularly methylester or lactone, for example γ-butyrolactone, gluconic acid lactone and glucopyranosylarabinoeic acid lactone. The use of very long-chained lactones, for example, 5-dodecanolide, is possible, but less preferred.

The use of acids with more than one carboxylic acid function, for example mucic acid or its epimer glucaric acid, is possible, but less preferred. By using difunctional carboxylic acids a specific increase of the molecular weight can be achieved by partial crosslinking.

Alternatively, at least one carboxylic acid group and esters comprising at least one hydroxyl group can be used for the introduction of the hydrophilic residue $R^9$. A preferred embodiment includes monoesters of dicarboxylic acids. Examples of dicarboxylic acids are oxalic acid, succinic acid, maleic acid, fumaric acid, phthalic acid, terephthalic acid. It lies within the bounds of the invention to esterify the carboxylic acids in the form of their anhydrides. The alcohols used for esterification are at least dihydroxy-functional alcohols with a chain length of ≥$C_3$ atoms. Examples of alcohols are 1,2-propane diol, 1,3-propane diol, glycerol, pentaerythrol and sorbitol.

It is within the scope of the invention to esterify the alcohols, in the form of their epoxides, for example propylene oxide, with the acids.

The use of tri- and higher functional carboxylic acids is possible, but less preferred. An example is trimellitic acid, which can be converted into a non-carboxylic acid diester structure particularly starting from trimellitic acid anhydridic acid chloride. Another example is pyromellitic acid dianhydride, which preferably forms a dicarboxylic acid diester structure. As already discussed, an increase of the molecular weight via partial crosslinking can be achieved by using at least difunctional carboxylic acids.

For introducing the hydrophilic elements $R^{10}$ the preferably epoxy functionalized intermediates, can be partially reacted with for example
  hydroxyl groups comprising primary or secondary amines or
  at least one primary or secondary amino group and at least one hydroxyl group comprising amino amides.

The hydroxyl groups containing primary or secondary amines are for example ethanolamine, diethanolamine, 1-amino-(2-hydroxy) propane, 1-amino-(3-hydroxy) propane, 1-amino-2,3-dihydroxy propane, glucamine, N-methylglucamine.

For introducing the lipophilic element $R^{11}$ the preferably epoxy functionalized intermediates are reacted with
  carboxylic acids or
  at least one carboxylic acid group comprising esters.

In the context of the invention fatty acids are understood to be monocarboxylic functional carboxylic acids. Examples of suitable fatty acids are acetic acid, caproic acid, 2-ethylcaproic acid, lauric acid, tetradecanoic acid, hexadecanoic acid, octadecanoic acid, undecenic acid, oleic acid, linoleic acid, linolenic acid.

For the introduction of the lipophilic residues $R^{11}$ preferably monocarboxylic functional carboxylic acids with $\geq C_{10}$ atoms are used, as these have a particularly strong bonding capacity to and solubility in the oil phase.

The use of acids with more than one carboxylic acid function, for example lauric diacid or dodecenyl succinic acid and their anhydrides respectively, is possible, but less preferred. The use of difunctional carboxylic acids can specifically achieve an increase of the molecular weight via partial crosslinking.

Alternatively, at least one carboxylic group comprising ester can be used for the introduction of the residue $R^{11}$.

They are monoesters of dicarboxylic acids in a preferred embodiment Examples of dicarboxylic acids are oxalic acid, succinic acid, maleic acid, fumaric acid, phthalic acid, terephthalic acid. It is within the bounds of the invention to esterify the carboxylic acids in the form of their anhydrides. The alcohols used for esterification are preferably monohydroxy functional alcohols. Examples of alcohols are ethanol, 2-propanol, 2-ethylhexanol, dodecanol, undecenol, isotridecanol, hexadecanol, oleyl alcohol, octadecanol, mono- and oligopropoxylates of monohydroxy functional alcohols, $HOCH_2CH_2(CF_2)_5CF_3$ and $HO(CH_2)_6Si(CH_3)_3$.

It is within the scope of the invention to esterify the alcohols in the form of their epoxides, for example dodecene oxide, with the diacids.

The use of tri- and higher functional carboxylic acids is possible, but less preferred.

An example is trimellitic acid, which can, starting from trimellitic acid anhydride acid chloride, be converted into a monocarboxylic diester structure. Another example is pyromellitic acid dianhydride, which preferably forms a dicarboxylic acid diester structure. As already discussed, a specific increase in the molecular weight can be achieved by the use of difunctional carboxylic acids via partial crosslinking.

The esterification of epoxides with carboxylic acids, if necessary in the presence of catalysts such as e.g. tertiary amines, is known (E. Sung, W. Umbach, H. Baumann, Fette Seifen Anstrichmittel 73, 1971, p. 88).

Preferably, the molar ratio of $\Sigma$epoxy groups:$\Sigma$acid groups+amino groups amounts to 1:1 to 1:2, preferably 1:1 to 1:1.5, especially 1:1 to 1:1.1. An excess of epoxy groups over acid+amino groups is possible but less preferred.

In order to regulate the characteristics of the polysiloxane copolymers according to the invention as O/W or W/O-emulsifiers, the ratios of the individual structural elements to one another is significant. These can, within the scope of the invention, be adapted to the chemical structure of the oil to be emulsified and the intended ratio water phase:oil phase.

An increase in the proportion of the conventional, non-modified "siloxane units". tends to result in, for example, a better compatibility with siloxane-based oil phases.

An increase in the proportion of the hydrophilic units tends to result in, for example, a better compatibility with the water phase.

An increase in the proportion of lipophilic units tends to result in, for example, a better compatibility with hydrocarbon-based oil phases.

It is within the scope of the invention to carry out the reactions for the production of the polysiloxane compounds in accordance with the invention without solvents or in the presence of solvents. Suitable solvents are, for example, water, esters or ester-comprising mixtures, such as ethyl acetate, butyl acetate, methoxypropyl acetate, ester aromatic substances, such as acetic acid esters of dicyclopentadiene, ether or ether-comprising mixtures, such as dipropylene glycol, propylene glycol monomethyl ether and dibutyl ether, ether aromatic substances, such as anisole, alcohols, such as ethanol, i-propanol, propylene glycol and glycerol. The optional choice of a solvent and its required quantity are inter alia dependent on the structure of the acid component and the intended application purpose. Thus, it can be advantageous to already perform the synthesis in a solvent, which is, for example, a component of the final W/O-formulation.

The reactions are preferably carried out in a temperature range between room temperature and 180° C., preferably between room temperature and 150° C., most preferably between 50° C. and 150° C.

The reaction times are determined by the complete reaction of epoxy, acid and amino groups. These can be easily observed by suitable methods (IR, NMR, Titration).

Preferred Applications

By changing the ratio of the siloxy units containing exclusively $R^{17}$ to $R^9$ and optionally $R^{10}$ and $R^{11}$ containing ones it is possible to alter the solubility characteristics considerably.

A specific advantage of the polysiloxane compounds according to the invention is that the incorporation of the dendrimeric moiety $R^9$ makes accessible strongly hydrophilic silicone compounds. It is another advantage that a certain hydrophilicity level can be reached by using a relatively small number of anchoring points only Remaining anchoring points can be used for modifications with $R^{10}$ and $R^{11}$ or can be replaced by standard siloxy units bearing exclusively $R^{17}$.

The hydrophilic compounds according to the invention feature, in comparison to pure polydimethylsiloxanes, an improved solubility in water and polar solvents, such as alcohols, other oxygen-, sulphur- and nitrogen-comprising hydrocarbons. They can be used as O/W emulsifier.

O/W-Emulsions

A typical O/W-emulsion in accordance with the invention is produced in that the oil phase is provided and the emulsifier or the emulsifiers are added to the oil phase. Subsequently, the water phase, optionally containing water soluble ingredients, is added by stirring. This process can, depending on the composition of the phases, be carried out cold as well as by heating. Subsequently, it is possible to follow up with a homogenisation step in order to possibly increase stability. Emulsions as well as microemulsions can be obtained following this protocol.

In this connection, a general O/W-emulsion according to the invention has the following composition in wt.-%:

| | |
|---|---|
| 0.1-20% | polysiloxanes according to the invention |
| 10-60% | oil phase |
| 0-10% | additives |
| 20-89.9% | water phase |

A broad spectrum of oil phases can be emulsified.

In this context the oil phase can comprise an oil or combinations of two or more oils and also further oil-compatible cosmetic raw materials. Oils, which are used in cosmetics, differ in their polarity. These can be, according to the literature (Cosmetology Theory and Practice; Volume 3, page 31, Table 10.2; Editors: K. Schrader, A. Domsch; Verlag für chemische Industrie, 2005), described by their surface tension (also defined as polarity index). A particular characteristic of the polysiloxane compounds according to the invention is that, in this connection, they are capable of stabilising emulsions with a great range of oil polarities. In this connection the preferred oil polarities represented by the polarity index lie in a range of between 4 and 55 mN/m, with the range between 13 and 39 mN/m being particularly preferred. In this connection it is self-evident that the values of the oil polarities lie in the preferred or more preferred range and can be achieved by mixing or blending two or more components. The following materials are named as possible components for the oil phase, by way of example but not limiting, wherein the materials can be introduced singly or in combinations of several components. Triglycerides are, for example, avocado oil, peanut oil, hydrogenated peanut oil, oat oil, mink oil, olive oil, castor oil, hydrogenated caster oil, shea butter oil, soy oil, sunflower oil, sesame oil, peach stone oil, wheat germ oil, macadamia nut oil and *oenothera biennis* oil.

Silicones such as volatile linear and cyclic polydimethyl siloxane (hexamethyl disiloxane, ethyl-, propyl and butyl disiloxane, diethyl-, dipropyl- and dibutyl disiloxane, octamethyl disiloxane, octamethyl trisiloxane, pentamethyl tetrasiloxane, dodecamethyl penta-siloxane, various ethyl and diethyltrisiloxanes, various propyl- and dipropyl trisiloxanes, various butyl trisiloxanes, various pentyl trisiloxanes, various hexyl trisiloxanes, cyclotetrasiloxanes, cyclopentasiloxanes, cyclohexasiloxanes, cycloheptasiloxanes and further variations), dimethicone (viscosity 3-100 kPa·s at 25° C. as well as blends of the different viscosities and solutions of dimethicones in volatile silicones and hydrocarbons), phenyl modified silicones (phenyltrimethicones and phenyldimethicones with different viscosities as well as blends thereof), alkyl- and aryl modified silicones (caprylylmethicones, stearyl-, cetyl-, cetearyl-, C26-C28-alkyl C30-C45-alkyl methicones and dimethicones, phenylpropyldimethylsiloxysilicate), polyether modified silicones (INCI: PEG-x/PPG-y dimethicones), amino functional silicones (amodimethicones), fluoroalkyl modified silicones, silicone resins (trimethylsiloxysilicate, polymethylsilsesquioxanes, diisostearyl trimethylolpropane siloxysilicates and trifluoropropyl/trimethylsiloxysilicates), silicone acrylates (dimethicone PEG-8 Polyacrylates) and silicone elastomers and silicone cross-polymers (dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer. PEG-15/lauryl dimethicone crosspolymer, PEG-10/lauryl dimethicone crosspolymer, dimethicone/polyglycerol-3 crosspolymer, lauryl dimethicone/polyglycerol-3 crosspolymer and dimethicone/vinyltrimethyl siloxysilicate crosspolymer).

Hydrocarbons such as for example paraffin oils with various viscosities, petroleum jelly, paraffins (hard and soft), microcrystalline waxes, ozocerites, ceresin, squalenes, squalanes and volatile, linear and/or branched hydrocarbons with 5 to 20 carbon atoms.

Fatty alcohols as consistency regulators such as, for example, lauryl-, myristyl-cetyl-, oleyl- and stearyl alkohol, and mono- and diglycerides of fatty acids.

Natural waxes and fats and those based on natural products such as Japanese wax, lanolin, cocoa butter, cetyl palmitate, beeswax (natural and synthetic), carnauba wax, candelilla wax and jojoba oil.

Fatty acid esters of monoalcohols such as isopropyl myristates, isopropyl palmitates, isopropyl stearates, oleyl oleates, decyl oleates and cetearyl ethylhexanoates.

A further preferred embodiment of the invention relates to the use of the hydrophilic or hydrophilic/lipophilic modified polysiloxane compounds according to the invention for the production of viscosity regulators, antistatic agents, mixture components for silicone rubbers which can be crosslinked to elastomers, either by peroxides or by hydrosilylation (platinum catalyst) and lead in that case to the modification of surface characteristics, the modification of the diffusion of gases, liquids, etc., modify the swelling characteristics of the silicone elastomers e.g. compared to water, respectively.

In particular, the use as an additive for the hydrophilization of the surfaces of polydimethylsiloxane elastomers in general, or as a viscosity regulator in non-crosslinked silicic acid-comprising silicone rubbers is preferred. Here silicone rubbers mean in particular low-viscosity moulding or sealing masses known as Room-Temperature-Vulcanizing (RTV) 1- or 2-component rubbers. For these RTV 1-C or 2-V rubbers the adjustment of high or low flow limits depending on the use, is desired. The organo-modified polydimethylsiloxane according to the invention is applied in amounts of from 0.5 to 15 wt. % relative to the silicone rubbers during the production of the rubber composition or to the surface of the elastomer.

They can also be applied onto the surface as lubricants by immersion, pouring or spreading and can be partially removed again by rubbing or rinsing after intended use or setting up.

A further preferred embodiment of the invention relates to the use of the hydrophilic or hydrophilic/lipophilic modified polysiloxane compounds according to the invention for the production of modifying agents for thermoplastic plastic materials such as polyolefins, polyamides, polyurethanes, poly(meth)acrylates and polycarbonates. This includes, in particular, the use as or production of low temperature impact resistant modifying agents.

For this the polysiloxane compounds themselves can be used directly as modifying agents or, however, also be prepared in advance by mixing, compounding or masterbatching production in a suitable form.

A further use of the copolymers according to the invention includes coatings, such as anti-fouling, non-stick coatings, body tissue compatible coatings and materials.

Further uses include anti-fogging coatings or the precursors for the production of these for headlight glass (inner surface), panes for residential buildings, for automobiles or medical equipment as well as additives for cleaning agents, detergents or preservative agents, as an additive for toiletries, as a coating agent for wood, paper and cardboard, as a mould release agent, as a biocompatible material for medicinal uses such as contact lenses, as a coating agent for textile fibres or textile fabrics, as a coating agent for natural materials such as e.g. leather and furs or fleeces.

The hydrophilic or hydrophilic/lipophilic modified polysiloxanes can also serve as cosmetics, toiletries, paint additives, additives in detergents, defoaming formulations and in textile processing.

In a preferred application the hydrophilic or hydrophilic/lipophilic modified polysiloxanes with a small proportion of $R^9$ are used for the defoaming of diesel oils and diesel fuels respectively, wherein the concentration of silicon in diesel oil is less than 5 ppm, more preferably less than 2 ppm.

A further preferred use is the application of the hydrophilic or hydrophilic/lipophilic modified polysiloxanes with a small proportion of $R^9$ as a foam stabilizer in cold or warm hardening polyurethane hard or flexible foams, preferably in amounts of from 0.5 to 5 wt. %, more preferably 1 to 3 wt % per applied polyol component with additional expanding agents whose boiling points lie between 60 and 50° C., such as, in particular, cyclopentane, iso-pentane, and/or iso-butane.

These uses comprise the production of softening agents for textile fibres, for the treatment of textile fibres before, during and after washing, of agents for the modification of natural and synthetic fibres, such as for example hair, cotton fibres and synthetic fibres, such as polyester fibres and polyamide fibres, as well as blended fabrics, finishing agents for textiles, as well as formulations comprising detergents, such as detergents or cleaning agents.

The preferred amounts in this case are 0.1 to 5 wt. %, 0.3 to 3 wt. %, corresponding to the fibre mass.

In an other preferred embodiment of the invention the hydrophilic or hydrophilic/lipophilic modified polyorganosiloxanes with a small proportion of $R^9$ are used as adjuvant in pesticides, agriculture, horticulture, turf, ornamental and forestry or emulsifier in compositions used therefore. These siloxane compounds preferably improve the dispersibility of active materials and stabilize the emulsions when diluted with more water.

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications, The pesticidal compositions of the present invention also include at least one pesticide, where the compounds of the present invention are present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides which ran be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compounds or compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the compounds of the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, munch, mancozeb, dodicin, dodine, and metalaxyl.

Insecticide, larvacide, mitiride and ovacide compounds that can be used with the composition of the present invention, but not limited to, *Bacillus Thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the compounds of the present invention, prior to application, and the compounds of the invention may act as a solvent, or surfactant for such solubility or additional surfactants may perform this function.

Agricultural Excipients:

Buffers, preservatives, carriers and other standard excipients known in the art also may include the compounds of the invention.

Solvents may also be included in compositions comprising the compounds of the present invention. These solvents are in a liquid state at room temperature (25° C.). Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,24-trimethyl, 1,3-pentanediol and alkoxylated (especially ethoxylated) versions thereof as illustrated in U.S. Pat. No. 5,674,832 herein incorporated by reference, or N-methyl-pyrrolidone.

Co-Surfactants:

Moreover, co-surfactants, which have short chain hydrophobes that do not interfere with superspreading as described in U.S. Pat. Nos. 5,558,806; 5,104,647; and 6,221,811 are herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL® from Air Products), pyrrilodone based surfactants (e.g., SURFADON®-LP 100-ISP), 2-ethyl hexyl sulfate, isodecyl alcohol ethoxylates (e.g., RHODASURF® DA 530-Rhodia), ethylene diamine alkoxylates (TETRONICS® BASF), and ethylene oxide/propylene oxide copolymers (PLURONICS® BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates, and so forth.

Use in Coatings and Paints:

In a further preferred embodiment of the invention the hydrophilic or hydrophilic/lipophilic modified polyorganosiloxanes of this invention are used in coating compositions. Typically coating formulations may include the compounds of the present invention as a wetting agent or surfactant for the purpose of emulsification, compatibilization of components, leveling, flow enhancement, deairing and the reduction of surface defects. Additionally, the compounds of the invention may provide improvements in the cured or dry film, such as improved abrasion resistance, antiblocking, hydrophilic, and hydrophobic properties. Coatings formulations may exist as, solvent-borne coatings, water-borne coatings and powder coatings.

The coatings components may be employed as Architecture coatings; OEM-product coatings such as automotive coatings and coil coatings; special purpose coatings such as industrial maintenance coatings and marine coatings, Typical resins include polymers of polyesters, alkyds, acrylics, epoxies, and polyurethanes.

A further preferred use is the application of hydrophilic or hydrophilic/lipophilic modified polysiloxanes with predominantly hydrophilic characteristics having a higher proportion $R^9$ as additives for the hydrophilization, improved wettability and antistatic finishing of thermoplastic and elastomeric surfaces. The preferred amounts in this case are 0.2 to 15 wt. %, 0.5 to 10 wt. % relative to the thermoplastic or elastomeric composition. Another preferred application of the hydrophilic or hydrophilic/lipophilic modified polysiloxanes is the use in the heat sensitized coagulation of rubber latex for the manufacture of e.g. gloves, condomes, balloons other latex based articles, whereby the solubility in the latex emulsion decreases when heated up to >35° C.; it prevents premature coagulation at room temperature.

Another preferred application is the use as demulsifiers in the oil and gas industry for faster and better separation of crude oil and water, as additive for anti-blocking, anti-fogging in order to prevent water droplets onto surfaces, mar resistance, as lubricant or lubricating additive, as tissue softeners or in tissue softener composition as self-emulsifying alkylylene oxide-free softener or as shear stable emulsifier in textile treatment formulations, as foam stabilizers for aqueous foams in detergents, dishwashing liquids and in general-purpose cleaners, as additives for hydrophilisation of plastic and thermoplastic or elastomer surfaces and the improved wettability of thermoplastic or elastomeric surfaces.

With respect to the above described usage as demulsifier and emulsion preventors in the oil and gas industry the following applications are preferred.

A. Mining and Petroleum Industry

The materials of the present invention may be utilized in mining and petroleum processing applications for foam control, including antifoaming in gas/oil or gas/oil/water separators, in oil processing, tank washing, distillation and other refinery operations, waste oil processing and in diesel fuel (including bio-diesel).

The materials of the present invention may be also utilized in mining and petroleum processing applications, as demulsifying and emulsion prevention agents. Using the materials of the present invention as a demulsifying agent is accomplished by
 i. incorporating a demulsifying-effective amount of at least one material of the present invention into an emulsion including crude-oil or the like;
 ii. allowing the emulsion to separate into at least two phases; and
 iii. separating said at least two phases from each other.

As is generally known, emulsions comprise at least two immiscible liquid phases, one of which is continuous and the other, which is discontinuous. Further, emulsions may also contain gases and solids.

One of the immiscible liquids in an emulsion is generally polar, and often water based and the other liquid is generally non-polar, generally defined as an oil phase.

The emulsion can be for example, a water-in-oil, an oil-in-water emulsion or a multiple phase emulsion. The emulsions particularly considered herein are those wherein the emulsified component is in the form of droplets with droplet sizes in the range of about 0.1 microns up to about 200 microns, more typically about 1-100 microns. The emulsified component can be unstabilized, but is more typically stabilized by a stabilizing amount of a surfactant and/or dispersed particulate solid. Further it is also possible to prepare emulsions of emulsions and these are generally known as multiple emulsions.

The aqueous phase can be essentially pure water, or alternatively, water with varying amounts of solid (particulate) materials, salt or other chemicals.

The oil phase is any hydrophobic phase substantially insoluble with the aqueous phase. For example, the oil phase can be composed of one or more hydrophobic chemicals, typically liquids, which individually or in combination are mainly insoluble in the aqueous phase. Such hydrophobic chemicals can be, for example, linear or branched, cyclic or acyclic, saturated or unsaturated, aliphatic or aromatic hydrocarbons. The hydrocarbons typically contain at least six carbon atoms and can be unsubstituted, or alternatively, substituted with one or more heteroatom-containing group (e.g., hydroxyl, amino, carboxyl, amide, anhydride, ester, or ether groups) as long as the hydrocarbons remain mainly insoluble with the aqueous phase.

Emulsions can create problems in many industrial applications because the emulsions often do not separate into the liquid components for a prolonged time, in this case typically chemical additives, so-called demulsifying agents, are added to initiate, accelerate and complete the separation process. Demulsifying agents break emulsions and mixtures of polar solutes like water, and non-polar solvents like oil.

Demulsifiers are used to separate emulsions into polar (typically water) and non-polar liquids by incorporating the demulsifying agent into the emulsion.

The inventive materials described in the present invention can be used as demulsifying agents alone or accompanied by additional silicone and/or organic demulsifiers and these components can be utilized in the form of a blend, a solution, a dispersion, or either an oil-in-water or a water-in-oil emulsion or microemulsion or the various demulsifying, agents can be added separately. When applied in solution suitable solvents can be selected from linear or branched, cyclic or acyclic, saturated or unsaturated, aliphatic or aromatic hydrocarbons, alcohol, ketones, esters, ethers and their blends or whatever solvent is commonly used in the particular application.

When the organic and/or silicone demulsifier is included, the weight ratio of the compositions of the present invention to the organic and silicone demulsifier is typically in the range of about 100:1 to about 1:1000, more typically in the range of about 5:1 to about 1:200.

The method of separating emulsions comprises the incorporation of a demulsifying-effective amount of demulsifier into the emulsion, allowing the emulsion to separate into at least two phases and separating these at least two phases from each other. The incorporation of the demulsifier into the emulsion to be separated can be achieved by any method known in the art for integrally mixing the demulsifier with the emulsion. The mixing procedure can use, for example, standard mixers, high-speed mixers or blenders, or shakers. The temperature can be unadjusted within room temperature limits (~20-30° C.), or adjusted as required, for example, to 40-150° C. for a suitable amount of time.

A typical application of the materials in the present invention is the separation of crude oil emulsions. During extraction and production of crude oil, water or brine gets emulsified into the crude oil yielding a water-in-oil emulsion, which can be unstabilized or stabilized by surface active materials, organic solids, such as asphaltenes and resins, or inorganic solids. This water-in-oil emulsion gives rise to several down-stream problems; corrosion during refinery processes and greater energy requirement to pump the more viscous emulsion are to name a few, Thus, demulsifiers are extensively used in the petroleum industry, to break water-in-oil and oil-in-water emulsions; and before transportation, refining or processing the water content of the crude oil has to be reduced to pipeline specification levels (typically less then 0.05-2%) and this is typically achieved by injecting demulsifiers into the well, into the crude oil stream, at the separation equipment or at any other suitable points.

The materials of the present invention di cause improved demulsifying action as demulsifying agents in the Mining and Petroleum Industry, both in the oil field and refineries, including, but not limited to desalters, bitumen extraction from oils sands (separating bitumen froth and solvent diluted bitumen emulsions); in the separation of waste oils, slop oils, sludges, such as oily waste from desalters, waste water skimmings, refinery and petrochemical plant waste (tank bottom washes, coker drum waste, "dirty bleeds" etc.), steel and aluminum industrial waste, including synthetic lubes, high lithium grease, lube oil from rollers, metalworking fluid waste and paper plant waste.

Dehazing (demulsification) of lubrication oils and lubrication oil waste, such as automotive waste (motor oil etc.), bunker oil are also possible applications of the materials of the present invention.

Another typical industrial use of the materials of the present invention is diesel fuel (including bin-diesel) dehazing when the demulsifier eliminates small amount of emulsified water from the diesel fuel and diesel fuel antifoaming.

A further typical industrial use of the materials of the present invention is as emulsion preventor, also called non-emulsifier. Emulsion formation can be a serious problem in the oil field when a water or polar liquid is injected into the formation, for example, in hydraulic fracturing, well completion, well stimulation, acidizing, workover, drilling with aqueous drilign fluids, water re-injection, etc. The water or polar liquid phase may contain many other components, for example acids, surfactants, wetting agents, alcohols, glycols, biocides, anti-corrosion additives, iron control agents, sludge control agents, proppants drag reducers etc.

If a stable emulsion forms during these operations it can plug the pores of the formation or disturb the operation or production and therefore the use of emulsion preventor (non-emulsifier) can be essential.

An emulsion preventor is typically added to the water or polar liquid phase, and the emulsion preventor (non-emulsifier) then prevents the emulsion formation between the water and oil phases or destabilizes the emulsion.

The inventive materials described in the present invention can be used as emulsion preventors alone or accompanied by additional silicone and/or organic emulsion preventors and these components can be utilized in the form of a blend, a solution, a dispersion, or either an oil-in-water or a water-in-oil emulsion or microemulsion or the various demulsifying agents can be added separately. When applied in solution suitable solvents can be used.

The materials of the present invention will improve ore recovery from milling operations. The addition of the present invention to mining processes such as flocculation, separation, purification, concentration, leaching & chemical extraction improves the separation of minerals from their gangue.

Further applications of the materials of the present invention in oil and gas include asphaltene dispersants and drag reduction.

Water-in-Oil Emulsions (W/O-Emulsions)

In another preferred embodiment the polysiloxanes of the invention are used as W/O emulsifiers. As already outlined earlier this can be achieved by a careful choice of the ratio between the moieties $R^9$ to $R^{17}$ (a preferred ratio is ≤0.2). The incorporation of a substantial number of moieties $R^{10}$ further improves this characteristic.

The ester units comprising polysiloxanes can in this case be used hereby as single components as well as combinations of various structures and, furthermore, in combination with other emulsifiers. W/O-emulsions generally comprise an external less polar phase, which hereinafter is referred to as the oil phase, an internal polar phase, which hereinafter is called the aqueous phase and an emulsifier or emulsifiers. Various raw materials can be introduced into the polar respectively non-polar phase.

Water Phase

In this connection, the aqueous phase of the described W/O emulsions can comprise water, alcohols and polyols such as for example glycerol and its ester, ethylene glycol, diethylene glycol and its ester, propylene glycol, dipropyplene glycol, butylene glycol and its ester, ethanol, isopropanol and sorbitol as well as combinations thereof. Furthermore, soluble substances, such as for example salts, active substances, preservatives, inorganic and organic dyes, oxidants and pH-regulators can be introduced into the aqueous phase.

Emulsifiers

The following emulsifiers can be used together with the polysiloxane compounds according to the invention respectively combinations thereof. Emulsifiers comprising polyalkylene oxide groups can also be used in the process, wherein they can be applied in lesser amounts by using the polysiloxane compounds in accordance with the invention, or they can be completely dispensed with.

Anionic emulsifiers such as metal soaps are fatty acid salts of polyvalent metals, such as for example the stearates, myristates, laureates or oleates of magnesium, zinc and aluminium.

Amphoteric emulsifiers are phospholipids and proteins such as lecithin and lactoproteins.

Non-ionic emulsifiers such as fatty alcohols, absorption or ointment bases on the basis of different raw materials such as petroleum jelly, paraffin, mineral oil, beeswax, lanolin, cholesterol and alcohols with a high molecular weight and esters thereof, lecithin and eucerite, (purified wool wax alcohol) are produced, wool wax alcohol and its fractions (in particular cholesterol), partial esters of multivalent alcohols with higher fatty acids, sterols as well as oleates, ricinolates and lanolates of sorbitane, pentaerythrit, glycerol and polyglycerol.

Silicone emulsifiers such as PEG-x/PPG-y dimethicone (x=0–100, y=0–100, x+y>1), alkyl PEG-x/PPG-y dimethicone (alkyl=linear and branched alkyl or aryl residues with 2-50 carbon atoms, x=0–100, y=0–100, x+y>1), polyglyceryl-x disiloxane dimethicone (x=2–10), polyglyceryl-x polydimethylsiloxyethyl dimethicone (x=2–10) and alkyl polyglyceryl-x polydimethylsiloxyethyl dimethicone Alkyl=linear and branched alkyl respectively aryl residues with 2-50 carbon atoms, x=2–10).

Particularly suitable emulsifiers, which can either be used alone or together in any combination with the polysiloxanes in accordance with the invention, are glyceryl oleate, glyceryl isostearate, sorbitane trioleate, sorbitane sesquioleate, sorbitane sesquiisostearate, sorbitane oleate, sorbitane isostearate, methyl glucose dioleate, methyl glucose sesquistearate, dicocoyl pentaerythrityl distearyl citrate, pentaerythrityl tetralaurate, polyglyceryl-2 sesquioleate, polyglyceryl-2 sesquiisostearate, polyglyceryl-3 sesquioleate, polyglyceryl-3 sesquiisostearate, polyglyceryl-4 oleate. PEG-4 oleate, PEG-6 dioleate, PEG-5 soy sterol, Peg-7 hydrogenated castor oil, oleth-2, oleth-3, isostereareth-2, isostearyl diglyceryl succinate, trioleyl phosphate, calcium stearoyl lactylate, laurylmethicone copolyol and cetyl dimethicone copolyol.

Oil Phase

In this connection the oil phase can comprise an oil or, however, combinations of two or more oils and also further oil-compatible cosmetic raw materials. Oils, which are used in cosmetics differ in their polarity. These can, according to the literature (Cosmetology—Theory and Practice; Volume 3, page 31, Table 10.2; Editors: K. Schrader, A. Domsch; Verlag für chemische Industrie, 2005), be described by their surface tension (also defined as polarity index). A particular characteristic of the polysiloxane compounds according to the invention is that, in this connection, they are capable of stabilising emulsions with a great range of oil polarities. In this connection the preferred oil polarities represented by the polarity index lie in a range of between 4 and 55 mN/m, with the range between 13 and 39 mN/m being particularly preferred. In this connection it is self-evident that the values of the oil polarities lie in the preferred or more preferred range and can be achieved by mixing or blending two or more components. The following materials are named as possible components for the oil phase, by way of example but not limiting, wherein the materials can be introduced singly or in combinations of several components. Triglycerides are, for example, avocado oil, peanut oil, hydrogenated peanut oil, oat oil, mink oil, olive oil, castor oil, hydrogenated caster oil, shea butter oil, soy oil, sunflower oil, sesame oil, peach stone oil, wheat germ oil, macadamia nut oil and oenothera biennis oil.

Silicones such as volatile linear and cyclic polydimethyl siloxane (hexamethyl disiloxane, ethyl-, propyl and butyl disiloxane, diethyl-, dipropyl- and dibutyl disiloxane, octamethyl disiloxane, octamethyl trisiloxane, pentamethyl tetrasiloxane, dodecamethyl penta-siloxane, various ethyl and diethyltrisiloxanes, various propyl- and dipropyl trisiloxanes, various butyl trisiloxanes, various pentyl trisiloxanes, various hexyl trisiloxanes, cyclotetrasiloxanes, cyclopentasiloxanes, cyclohexasiloxanes, cycloheptasiloxanes and further variations), dimethicone (viscosity 3-100 kPa.s at 25° C. as well as blends of the different viscosities and solutions of dimethicones in volatile silicones and hydrocarbons), phenyl modified silicones (phenyltrimethicones and phenyldimethicones with different viscosities as well as blends thereof), alkyl- and aryl modified silicones (caprylylmethicones, stearyl-, cetyl-, cetearyl-, C26-C28-alkyl C30-C45-alkyl methicones and dimethicones, phenylpropyldimethylsiloxysilicate), polyether modified silicones (INCI: PEG-x/PPG-y dimethicones), amino functional silicones (amodimethicones), fluoroalkyl modified silicones, silicone resins (trimethylsiloxysilicate, polymethylsilsesquioxanes, diisostearyl trimethylolpropane siloxysilicates and trifluoropropyl/trimethylsiloxysilicates), silicone acrylates (dimethicone PEG-8 Polyacrylates) and silicone elastomers and silicone cross-polymers (dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerol-3 crosspolymer, lauryl dimethicone/polyglycerol-3 crosspolymer and dimethicone/vinyltrimethyl siloxysilicate crosspolymer).

Hydrocarbons such as for example paraffin oils with various viscosities, petroleum jelly, paraffins (hard and soft), microcrystalline waxes, ozocerites, ceresin, squalenes, squalanes and volatile, linear and/or branched hydrocarbons with 5 to 20 carbon atoms.

Fatty alcohols as consistency regulators such as, for example, lauryl-, myristyl-cetyl-, oleyl- and stearyl alkohol, and mono- and diglycerides of fatty acids.

Natural waxes and fats and those based on natural products such as Japanese wax, lanolin, cocoa butter, cetyl palmitate, beeswax (natural and synthetic), carnauba wax, candelilla wax and jojoba oil.

Fatty acid esters of monoalcohols such as isopropyl myristates, isopropyl palmitates, isopropyl stearates, oleyl oleates, decyl oleates and cetearyl ethylhexanoates.

Stabilizers

A particularly important substance group for use in the external phase are so-called stabilisers, which can be very important for the production of stable emulsions. These substances are generally incorporated in the oil phase and form gel-like structures. Particularly suitable for this purpose are fatty alcohols such as e.g. lauryl-, myristyl-cetyl-, oleyl- and stearyl alcohol, hydrocarbon and polymer gels such as e.g. vaseline and polyethyls, paraffin wax (microcrystalline wax), wax esters such as e.g. cetyl palmitate, beeswax and substitutes, carnuba wax and candelilla wax, lanolin, multivalent metal soaps of fatty acids such as e.g. zinc- and magnesium ricinoleate as well as alkaline earth lanolates, calcium- and magnesium soaps and stearate soaps of multivalent metals, bentonite and modified bentonite, EO-PO-block copolymers such as e.g. PEG-22/dodecyl glycol copolymer, PEG-40/dodecyl glycol copolymer, and poloxamer types from BASF, silicone waxes such as stearyl-, cetyl-, cetearyl-, C26-C28-alkyl, C30-C45-alkyl methicone and dimethicone and silicone elastomers and silicone crosspolymers such as e.g. dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerol-3 crosspolymer, lauryl dimethicone/polyglycerol-3 crosspolymer and dimethicone/vinyltrimethyl siloxysilicate crosspolymer.

Consistency Agents

Consistency agents are monovalent, primary alcohols with a carbon chain length of more than 4 C-atoms such as lauryl-, myristyl-, cetyl-, stearyl-, oleyl and cetyl alcohol as well as mixtures thereof, mono- and diglycerides of fatty acids, natural waxes and those based on a natural basis, such as Japanese wax (*Cera japonica*), lanolin, cocoa butter, cetyl palmitate, beeswax (white, bleached and synthetic), carnauba wax, candelilla wax and jojoba oil, fatty acid esters of monovalent alcohols such as isopropyl myristates, isopropyl palmitates, isopropyl stearates, oleyl oleates, decyl oleates and cetearyl ethylhexanoates, silicone waxes such as stearyl-, cetyl-, cetearyl-, C26-C28-alkyl, C30-C45-alkyl methicones and dimethicones and silicone elastomers and silicone crosspolymers such as e.g. dimethicones/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerin-3 crosspolymer, lauryl dimethicone/polyglycerin-3 crosspolymer and dimethicone/vinyltrimethyl siloxysilicate crosspolymer.

Active Substances or Active Ingredients for Skincare Products

Suitable active ingredients for the production of W/O-emulsions with the polysiloxane compounds according to the invention are propolis or propolis wax, which is used because of its antimicrobial and antioxidative effect of the flavonoids comprised therein, Royal Jelly, which is suitable as a nurturing additive because of its high content of vitamins, amino acids, sugars, enzymes and biopeptin, collagen for stabilising the moisture of the stratum corneum, collagen hydrolysate for the improvement of skin and mucous membrane tolerance, elastin hydrolysate (hydrolysed elastin) alone or in combination with soluble collagen for the improvement of skin elasticity by hydration, phytosterols (avocado oil unsaponifiables, soy bean oil unsaponifiables) for a positive effect on the skin's connective tissue, vitamins such as vitamin A (retinol, retinyl acetate, retinyl palmitate and retinyl propionate) for the treatment and prevention of dry, rough, cornified and aging skin and atrophy of the perspiratory glands, beta-carotene which in the form of provitamin A exhibits the same effects as vitamin A, vitamin E (tocopherol, tocopherol acetate and tocopherol nicotinate) because of its antioxidative effect, improvement of the structure of the skin's surface, increase of the moisture-retaining properties of the corneum, the anti-inflammatory effect, acceleration of the epithelisation of superficial wounds, increase in the enzyme activity of the skin and boosting the blood circulation of the skin, pyridoxin or pyridoxin.HCl (vitamin B6) for the treatment of pellagra particularly in combination with essential fatty acids, niacin or niacin amides for the treatment of pellagra and of skin changes caused by deficiency symptoms, biotin (vitamin H) for the treatment of hair loss and anti-seborrhoic vitamin panthenol or d-panthenol and calcium panthenate for the improvement and increase of the moisture-retaining properties of the skin, for the inhibition of inflammation and itching, for the stimulation of epithelisation (accelerated healing of wounds), and for the improvement of the condition of damaged hair, vitamin C (ascorbic acid, sodium ascorbate and ascorbyl palmitate) because of its antioxidative effect and for the reduction of nitrosamine formation, essential fatty acids such as vitamin F (linoleic acid (and) linolenic acid (and) archidonic acid), vitamin-F-glycerol ester (glyceryl linoleic acid (and) glyceryl linolenic acid (and) glyceryl archidonic acid) and Vitamin-F-ethyl ester (ethyl linoleic acid (and) ethyl linolenic acid (and) ethyl archidonic acid) for the treatment of deficiency symptoms caused by a deficiency of linoleic acid such as dry, scaly skin rash, ceramide for the increase of moisture in the stratum corneum, anti-inflammatory substances such as bisabolol, camomile extracts, panthenol, glycyrrhizinic acid, witch hazel extract and certain peptides, ceratene-hardening substances which react with the proteins in the upper skin layers and thus to some extent seal it, such as formaldehyde or but also potassium aluminium sulfate, aluminium hydroxychloride, aluminium lactate, sodium aluminium chlorohydroxy acetate and aluminium circonium tetrachlorohydrate-glycin complex which clog up the capillaries and also the perspiratory glands, antimicrobial substances, hyperemic substances which stimulate blood flow such as essential oils such as mountain pine oil, lavender, rosemary, juniper, horse chestnut extract, birch leaf extract, cornflower extract, ethyl acetate, nettle extract, camphor, menthol, nicotinic acid and derivatives, peppermint oil, *eucalyptus* oil and turpentine oil, liposomes for increasing skin penetration, glycolipids such as glycerol glyco-lipids, glycosphingolipids (neutral glyco-sphingolipids, sulfatides and gangliosides) and cerebrosides, lipoproteins and zinc oxide for anti-inflammation.

Micro Pigments

Micro pigments are also called UV-blockers. They are characterized in that they are insoluble in the oil and the aqueous phases of the emulsion and offer UV protection in that they reflect and disperse UV light independently of their size. In this connection attention must also be paid to the fact that that with a decreasing particle size the "whitening" effect of pigment residues on the skin are reduced. Mainly magnesium oxide, calcium carbonate, magnesium carbonate, bentonite, titanium dioxide and zinc oxide are used. Titanium dioxide and zinc oxide are the most frequently used, with the use of zinc oxide being favoured because of its additional anti-inflammatory effect. Of late organic compounds are also used as micro pigments. An example of this is bis-ethylhexyloxyphenyl triazine (Tinosorb S, Ciba). When using micro pigments it is important that they are easily dispersed in the incorporated phase in order to ensure an ideal covering of the skin, which then results in a more effective UV protection. For this the above-mentioned pigments are also used as surface-treatment materials or as pre-dispersions. For the production of dispersions all substances, which have already been mentioned above as components for the oil phase or the aqueous phase can be used. The surface treatment also results from these substances. Furthermore, for the surface treatment dimethicones, simethicone and cylic silicones and emulsions thereof, hexamethyldisiloxane, hexamethyldisiloxane, alkyl- and aryl-functionalised silicones with alkyl- or aryl residues comprising 2 to 50 C-atoms, methyl-, alkyl- and aryl-functionalised alkoxy or halogen silanes with alkyl- or aryl residues comprising 2 to 50 C-atoms or polyether-modified silicones are frequently used.

The micro pigments can be introduced singly or also in combinations. A combination with the following UV filters for optimising the UV protection is also possible.

UV Filters

UV filters are substances, which selectively absorb UVA and/or UVB radiation.

Depending on the requirement profile, UV filters can be combined together and/or with micro pigments. Lists of suitable UV filters can be found in the "International Cosmetic Ingredient Dictionary and Handbook" Eleventh Edition 2006, Volume 3, page 2881 and "Cosmetology— Theory and Practice" Volume 3, pages 161-168; Editors: K. Schrader, A. Domsch; Verlag für Chemische Industrie, 2005.

Skin Tanning Agents

In this connection, examples of substances which tan the skin to be named are dihydroxyacetone, DHA and walnut extract.

Skin Bleaching Agents

Skin bleaching agents are used for the treatment of age spots or freckles. Active substances which can be used for producing cosmetic compositions with the aid of the polysiloxane compounds in accordance with the invention are hydroquinone, ascorbic acid, various peroxides, 5-hydroxy-2-(hydroxymethyl)-4H-pyran-4-on, 4-hydroxyphenyl-β-D-glucopyranosides and plant extracts. Further substances can be found in the "International Cosmetic Ingredient Dictionary and Handbook" Eleventh Edition 2006, Volume 3, page 2814.

Colorants and Dye Pigments

A list of suitable colorants and pigments can be found in the "International Cosmetic Ingredient Dictionary and Handbook" Eleventh Edition 2006, Volume 3, pages 2670-2677 and "Cosmetology—Theory and Practice" Volume 3, pages 222-223; Editors: K. Schrader, A. Domsch; Verlag für Chemische Industrie, 2005.

Further Fillers

This is understood to include particles and solids which influence light reflection and in this connection increase the proportion of the diffusely reflected light. Thus a soft focus effect is achieved which allows the skin to appear smoother and less wrinkled. Suitable additives are polymethyl silsesquioxanes, bornitride, nylon (Nylon-12), polyethylene (plastic powder), polyethylene/PTFE, dimethicone/vinyl dimethicone crosspolymer (and) lauroyl lysine, dimethicone/vinyl dimethicone crosspolymer (and) alumina, dimethicone/vinyl dimethicone crosspolymer (and) titanium dioxide, dimethicone/vinyl dimethicone crosspolymer, dimethicone/vinyl dimethicone crosspolymer (and) silica, polymethyl methacrylate, silica and silica silylate. These substances are also suitable for the absorption of sebum, which reduces skin shine.

Insect Protecting Agents

Suitable ingredients are inter alia ethyl butylacetylaminopropionate, diethyl toluamide and IR3535 Insect repellent by Merck.

Deodorants and Antiperspirants

Suitable ingredients for the production of antiperspirants with the polysiloxane compounds of the invention are fragrances, fragrance oils, triclosane, chlorhexidine, sodium hydrogen carbonate, clathrates such as zinc ricinolate and others, ion exchangers, triethylcitrate, o-acyl serine, acyl actylate, aluminium hydroxychloride, sodium aluminium chlorhydroxylactate, aluminium hydroxychloride with propylene glycol and circonium salts such as e.g. z.B. aluminium zirconium tetrachlorohydrex gly and aluminium circonium trichlorohydrex gly. Further antiperspirant active substances are mentioned in "Cosmetology—Theory and Practice" Volume 2, pages 268-269; Editors: K. Schrader, A. Domsch; Verlag für Chemische Industrie, 2005. A special form of antiperspirants is clear gels. These can be produced with the polysiloxane compounds according to the invention by matching the refraction indexes of the water and oil phases.

Ingredients for Hair Products

The polysiloxane compounds according to the invention are also suitable for the production of W/O-emulsions for hair care. In particular "leave-in" conditioners such as hair conditioners, hair gels, styling gels, hair forming agents, hair bleaching agents and hair colorants are to be mentioned here. The ingredients used in these compositions can be found in "Cosmetology—Theory and Practice" Volume 2; Editors: K. Schrader, A. Domsch; Verlag für Chemische Industrie, 2005.

Additives

Additives as ingredients for cosmetic formulations are defined in: A. Domsch, Die kosmetischen Präparate, Verlag für chem. Industrie, 4. Auflage, 1992; and in: Kosmetikjahrbuch 1995, Verlag für Chemische Industrie, 1995.

The following suitable additives are exemplary but, however, not limiting, as ingredients for the formulations: inorganic and organic acids, bases and buffers, salts, alcohols such as e.g. ethanol, isopropanol, ethylene glycol, polyethylene glycol, propylene glycol, poly-propylene glycol, glycol ether and glycerol, thickeners, stabilisers for emulsions such as e.g. xanthan gum, emollients, preservatives, foam stabilisers, defoamers, pearlescents and opacifiers such as e.g. glycol distearate and titanium dioxide, collagen hydrolysate, keratin hydrolysate, silk hydrolysate, anti-dandruff agents such as e.g. zinc pyrithion, salicylic acid, selenium disulfide, sulphur and tar preparations, polymer emulsifiers, vitamins, dyes, UV filters, bentonites, perfume oils, fragrances, styling polymers, moisturizers, plant extracts and further natural and nature-identical raw materials.

The preferred use of the substances according to the invention is the use for the production of cosmetic compositions for the treatment of substances comprising keratin, such as the human skin or human hair. In this connection specific cosmetic formulations for the use of the polysiloxane compounds according to the invention are creams and lotions for face and body care, creams and lotions for UV radiation protection, self-tanners, skin lighteners and products for the treatment of hyperpigmentation such as age spots and freckles (skin whiteners), make-up removers, pigmented products such as mascaras, eyeliners, lipsticks and liquid make-up (liquid foundation), deodorants and antiperspirants such as e.g. gels, roll-ons, creams and emulsions, "leave-in" conditioners for the hair such as e.g. deep hair conditioners and cures and gels, hair styling products such as e.g. hair gels, styling mousses and creams and hair waxes, hair bleaching agents, hair forming agents, hair waving agents, hair colorants. The substances according to the invention are suitable for use as W/O-emulsions and can of course also be used in multiple emulsions.

A typical W/O-emulsion in accordance with the invention is produced in that the oil phase is provided and the emulsifier or the emulsifiers are added to the oil phase. Subsequently, the water phase is added by stirring. This process can, depending on the composition of the phases, be carried out cold as well as by heating. Subsequently, it is possible to follow up with a homogenisation step in order to possibly increase stability. With this procedure all the above-mentioned oil-compatible substances are dissolved or dispersed in the oil phase, whereas hydrophilic substances are incorporated into the water or polar phase.

In this context, a general W/O-emulsion according to the invention has the following composition in wt.-%:

| | |
|---|---|
| 0.1-20% | polysiloxanes according to the invention |
| 10-60% | oil phase |
| 0-10% | additives |
| 20-89.9% | water phase |

The following compositions were found to be particularly advantageous for the use of the polysiloxane compounds according to the invention in cosmetic formulations:

A typical composition for a W/O-cream according to the invention, which, however, does not limit the invention, comprises the following components in wt.-%:

| | |
|---|---|
| 0.2-10% | polysiloxane compounds according to the invention |
| 0-5% | Co-emulsifiers |
| 5-55% | oil or a combination of oils |
| 0-10% | stabilisers |
| 0-10% | consistency agents |
| 0-20% | active substances or active ingredients for skin care products |
| 0-10% | further fillers |
| 0-10% | adjuvants |
| up to 100% | completed with water. |

A specific composition of a W/O-cream, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or a combination of oils |
| 0-5% | stabilisers |
| 0-5% | consistency agents |
| 0-20% | active substances or active ingredients for skin care products |
| 0-10% | further fillers |
| 0-10% | adjuvants |
| up to 100% | completed with water. |

A typical composition of a W/O-lotion according to the invention, which, however, does not limit the composition of the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | active substances or active ingredients for skin care products |
| 0-10% | further fillers |
| 0-10% | adjuvants |
| up to 100% | completed with water. |

A specific composition of a W/O-lotion, which, however, does not limit the invention, comprises the following components in wt.-%

| | |
|---|---|
| 0.5-6% | polysiloxane compounds according to the invention |
| 0-3% | Co-emulsifiers |
| 15-40% | oil or combination of oils |
| 0-5% | stabilisers |
| 0-5% | consistency agents |
| 0-20% | active substances or active ingredients for skin care products |
| 0-10% | further fillers |
| 0-10% | adjuvants |
| up to 100% | completed with water. |

A typical W/O-sunscreen cream composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A specific W/O-sunscreen cream composition, which, however, does not limit the invention, comprises the following components in wt.-%:

| | |
|---|---|
| 0.5-6% | polysiloxane compounds in accordance with the invention |
| 0-3% | Co-emulsifiers |
| 10-40% | oil or combination of oils |
| 0-5% | stabilisers |
| 0-5% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A typical W/O-sunscreen lotion composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-45% | oil or combination of oils |
| 0-10% | stabilisers |
| 0-10% | consistency agents |
| 0-20% | micro pigments |
| 0-20% | UV filters |
| 0-20% | active substances or active ingredients for skin care products |
| 0-10% | further fillers |
| 0-10% | adjuvants |
| up to 100% | completed with water. |

A specific W/O-sunscreen lotion composition, which, however, does not limit the invention, comprises the following components in wt.-%:

| | |
|---|---|
| 0.5-6% | polysiloxane compounds according to the invention |
| 0-3% | Co-emulsifiers |
| 15-40% | oil or combination of oils |
| 0-5% | stabilisers |
| 0-5% | consistency agents |
| 0-20% | micro particles |
| 0-20% | UV filters |
| 0-20% | active substances or active ingredients for skin care products |
| 0-10% | further fillers |
| 0-10% | adjuvants |
| up to 100% | completed with water. |

A typical W/O-self-tanner composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oil |
| 0-10% | stabilisers |
| 0-10% | consistency agents |
| 0.5-15% | skin tanning agents |
| 0-10% | active substances or active ingredients for skin care products |
| 0-10% | further fillers |
| 0-10% | adjuvants |
| up to 100% | completed with water. |

A specific W/O-self-tanner composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 1-15% | skin tanning agents |
| 0-10% | active substances or active ingredients for skin care products |
| 0-10% | further fillers |
| 0-10% | adjuvants |
| up to 100% | completed with water. |

A typical W/O-skin brightener composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0.5-15% | skin bleaching agents |
| 0-10% | active substances or active ingredients for skin care products |
| 0-10% | further fillers |
| 0-10% | adjuvants |
| up to 100% | completed with water. |

A specific W/O-skin brightener composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 1-15% | skin bleaching agents |
| 0-10% | active substances or active ingredients for skin care products |
| 0-10% | further fillers |
| 0-10% | adjuvants |
| up to 100% | completed with water. |

A typical liquid W/O-make-up composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-10% | stabilisers |
| 0-10% | consistency agents |
| 0-20% | UV filters |
| 2-20% | colorants and dye pigments |
| 0-10% | active substances or active ingredients for skin care products |
| 0-10% | further fillers |
| 0-10% | adjuvants |
| up to 100% | completed with water. |

A specific liquid W/O-skin make-up composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 0-5% | stabilisers |
| 0-5% | consistency agents |
| 4-15% | colorants and dye pigments |
| 0-20% | UV filters |
| 0-10% | active substances or active ingredients for skin care products |
| 0-10% | further fillers |
| 0-10% | adjuvants |
| up to 100% | completed with water. |

A typical W/O-mascara composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 2-20% | colorants and dye pigments |
| 0-10% | further fillers |
| 0-10% | adjuvants |
| up to 100% | completed with water. |

A specific W/O-mascara composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 2-20% | stabilisers |
| 2-20% | consistency agents |
| 4-15% | colorants and dye pigments |
| 0-10% | active substances or active ingredients for skin care products |
| 0-10% | further fillers |
| 0-10% | adjuvants |
| up to 100% | completed with water. |

A typical W/O-anti-perspirant composition according to the invention, which, however, does not limit the invention, comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 2-60% | antiperspirant (active substance) |
| 0-10% | adjuvants |
| up to 100% | completed with water. |

A specific W/O-anti-perspirant composition, which, however, does not limit the invention, comprises the following components in wt.-%:

| | |
|---|---|
| 0.5-6% | polysiloxane compounds according to the invention |
| 0-3% | Co-emulsifiers |
| 10-40% | oil or combination of oils |
| 2-20% | stabilisers |
| 2-20% | consistency agents |
| 5-50% | anti-perspirant (active substance) |
| 0-10% | active substances or active ingredients for skin care products |
| 0-10% | adjuvants |
| up to 100% | completed with water. |

A typical W/O-hair treatment agent composition according to the invention, which, however, does not limit the invention, for conditioning (softening and improving the wet and dry combing potential), for hair-styling, for smoothing, curling, bleaching or colouring the hair comprises the following components in wt.-%:

| | |
|---|---|
| 0.2-10% | polysiloxane compounds according to the invention |
| 0-5% | Co-emulsifiers |
| 10-50% | oil or combination of oils |
| 0-20% | stabilisers |
| 0-20% | consistency agents |
| 0.1-20% | ingredient for hair products |
| 0-10% | adjuvants |
| up to 100% | completed with water. |

EXAMPLES

The following examples are supposed to explain the invention in more detail, without, however, limiting it.

Preparation of Intermediate Materials 1-5

Preparation of Intermediate Material 1

Oligomerization of 2,2-bis-(hydroxymethyl) propionic acid 20 g (0.15 mol) 2,2-bis-(hydroxymethyl) propionic acid (BHMPA), 15 g distilled water and 0.03 g concentrated $H_2SO_4$ were mixed in a 100 ml three necked bottle, equipped with magnetic stirrer, thermometer, distillation bridge and $N_2$ inlet. A constant flow of $N_2$ was applied to remove the water from the bottle. The mixture was heated up. It turned into a transparent solution at 75° C., the water started to distill at 100° C. and was taken out of the bottle with the $N_2$ stream. The remaining material crystallized yielding a white mass. Upon further heating to approx. 138° C. the solid turned into a transparent glass like and viscous material. From this point on (t=0) time is counted. The temperature was kept at approx. 138 to 142° C. for in total 5 hrs. Samples were taken for NMR analysis in order to determine the degree on oligomerization of the structure

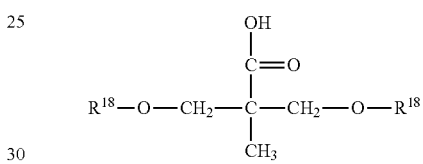

with
$R^{18}$=H or

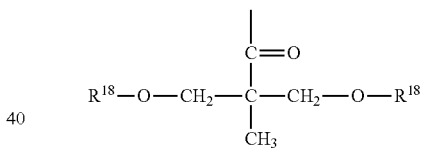

The following table summarizes the results of Preparation of Intermediate Material 1:

| time (min) | oligomerization | time (min) | oligomerization |
|---|---|---|---|
| 10 | dimer | 150 | octamer |
| 20 | trimer | 180 | octamer |
| 30 | tetramer | 210 | nonamer |
| 60 | hexamer | 240 | decamer |
| 90 | heptamer | 270 | decamer |
| 120 | heptamer | 300 | decamer |

Preparation of Intermediate Material 2

Oligomerization of 2,2-bis-(hydroxymethyl) propionic acid in water 2,2-bis-(hydroxymethyl) propionic acid (BHMPA), water and concentrated $H_2SO_4$ were mixed in a 100 ml three necked bottle, equipped with a magnetic stirrer. The bottle was closed, immersed into an oil bath having a temperature of 115° C. and maintained there for several hours. Depending on the ratio 2,2-bis-(hydroxymethyl) propionic acid: water the mixtures turned transparent after a few minutes (high water concentration) or after several hours (low water concentration). After the end of the reaction samples were taken, neutralized with tributylamine and analyzed by means of 1H-NMR. The signal ratio —C$\underline{H}_2$ OH:—C$\underline{H}_2$OC(O)— was taken as the measure for the degree on oligomerization (esterification).

The quantities of the reactants, reaction times and degrees on oligomerization are summarized in the following table:

| Samples | Preparation of Intermediate Material 2(a) | Preparation of Intermediate Material 2(b) | Preparation of Intermediate Material 2(c) | Preparation of Intermediate Material 2(d) |
|---|---|---|---|---|
| BHMPA (g) | 25 | 25 | 25 | 25 |
| water (g) | 25 | 6.25 | 2.77 | 1.31 |
| H$_2$SO$_4$ (g) | 0.04 | 0.04 | 0.04 | 0.04 |
| react. time (h) | 19 | 18 | 28 | 18 |
| ratio —C$\underline{H}_2$OH:—C$\underline{H}_2$OC(O)— | 11.7 | 2.83 | 2.09 | 1.82 |
| type oligomer | monomer + dimer | dimer | trimer | trimer + tetramer |

Preparation of Intermediate Material 3

Oligomerization of 2,2-bis-(hydroxymethyl) propionic acid and glycolic acid in water 24.12 g (0.18 mol) 2,2-bis-(hydroxymethyl) propionic acid (BHMPA), 1.52 g (0.02 mol) glycolic acid, 6.41 g water and 0.1 g concentrated H$_2$SO$_4$ are mixed in a 100 ml three necked bottle, equipped with a magnetic stirrer. The bottle is closed, immersed into an oil bath having a temperature of 115° C. and maintained there for 8 hours. The catalyst is neutralized with tributylamine and the product analyzed by means of 1H-NMR. The signal ratio —C$\underline{H}_2$OH (BHMPA):—C$\underline{H}_2$OC(O)— is taken as the measure for the degree on oligomerization (esterification).

Preparation of Intermediate Material 4

Oligomerization of 2,2-bis-(hydroxymethyl) propionic acid-dimer

Based on the reaction described in example 1a) a dimer was synthesized which contains one ester bond.

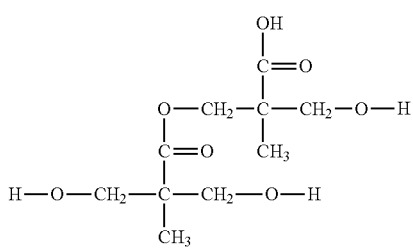

The material was cooled down to room temperature after the oligomerization. The candy like material was mixed with propylene glycol monomethylether and the mixture homogenized in the refluxing solvent (aprox. 120° C.). A 46.9% active dispersion of the dimer in propylene glycol monomethylether was obtained.

Preparation of Intermediate Material 5

Oligomerization of 2,2-bis-(hydroxymethyl) propionic acid-pentamer

Based on the reaction described in example 1 a pentamer was synthesized which contains four ester bonds

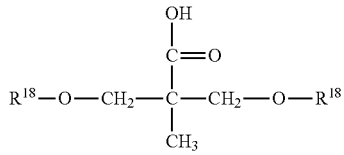

with $R^{18}$=H or

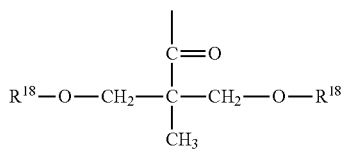

The material was cooled down to room temperature after the oligomerization. The candy like material was mixed with propylene glycol monomethylether and the mixture homogenized in the refluxing solvent (aprox. 120° C.). A 48.2% active dispersion of the pentamer in propylene glycol monomethylether was obtained.

Comparative Examples 1-2

Comparative Example 1

Production of a Copolymer Comprising Lactic Acid Ester Units 19.6 g (217.1 mmol) DL-lactic acid, 0.45 g triethyl amine and 70 g (211 mmol epoxy groups) of a siloxane of the structure

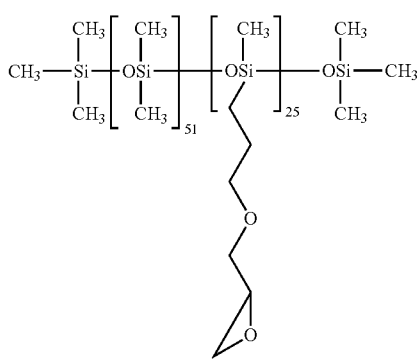

were dissolved in 38.4 g propylene glycol monomethylether. The mixture was heated to 120° C. for 10 hours. The epoxide conversion is determined by means of NMR (99.3%).

Afterwards, 80 g water were added. The azeotrope water/propylene glycol monomethylether and some excess water were distilled off at approximately 95° C. to finally 100° C.

A transparent solution of the target polymer in water having an active level of 90.6% was obtained.

The approximate structure is

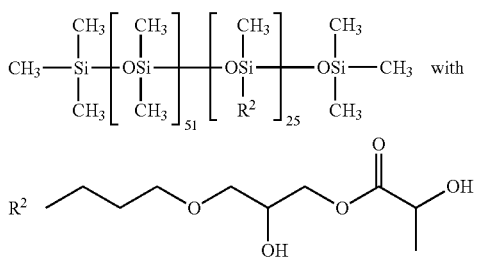

Comparative Example 2

Production of a copolymer comprising 2,2-bis-(hydroxymethyl) propionic acid ester units 29 g (216. mmol) 2,2-bis-(hydroxymethyl) propionic acid, 0.5 g triethyl amine and 70 g (211 mmol epoxy groups) of a siloxane of the structure

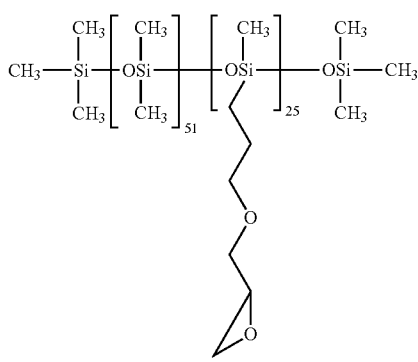

were dissolved in 231 g propylene glycol monomethylether. The mixture was heated to 120° C. for 15 hours. The epoxide conversion was determined by means of NMR (92.4%).

Afterwards, 700 g water were added. The azeotrope water/propylene glycol monomethylether and some excess water were distilled off at approximately 95 OC to finally 100° C.

An opaque solution of the target polymer in water having an active level of 71.3% was obtained.

The approximate structure is

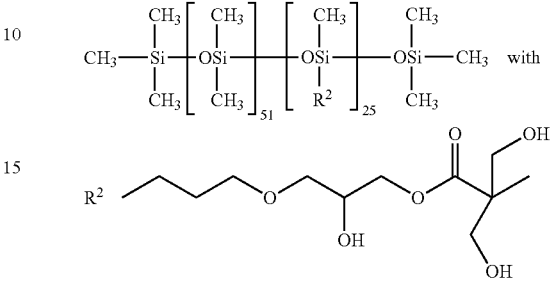

Inventive Examples 1-14

Example 1

Production of a Copolymer Comprising Dimer Based Units 26.4 g (49.4 mmol COOH) of the 46.9% active dimer dispersion from example 2, 0.5 g triethyl amine and 16.4 g (49.4 mmol epoxy groups) of a siloxane of the structure

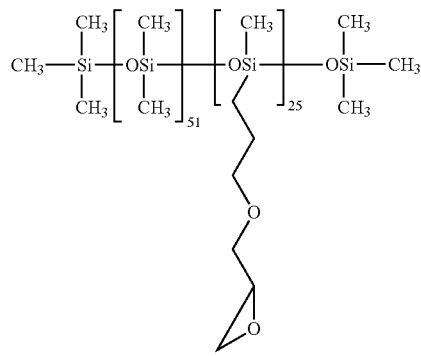

were dissolved in 99.9 g propylene glycol monomethylether. The mixture was heated to 120° C. for 24 hours. The epoxide conversion was determined by means of NMR (95.6%).

Afterwards, 200 g water were added. The azeotrope water/propylene glycol monomethylether and some excess water were distilled off at approximately 95° C. to finally 100° C.

An opaque solution of the target polymer in water having an active level of 75% was obtained.

Approximate structure is:

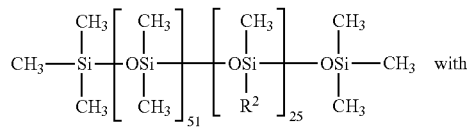

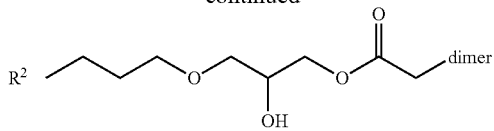

Example 2

Production of a Copolymer Comprising 2,2-bis-(hydroxymethyl) propionic Acid Ester Units and Dimer Based Units 5.3 g (39.5 mmol) 2,2-bis-(hydroxymethyl) propionic acid, 5.65 g (11.2 mmol COOH) of the 46.9% active dimer dispersion from example 2, 0.5 g triethyl amine and 16.4 g (49.4 mmol epoxy groups) of a siloxane of the structure

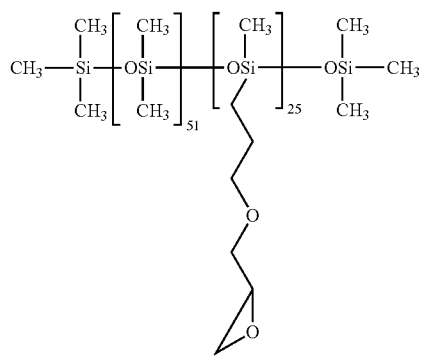

were dissolved in 63.8 g propylene glycol monomethylether. The mixture was heated to 120° C. for 12 hours. The epoxide conversion was determined by means of NMR (98%).

Afterwards, 120 g water were added. The azeotrope water/propylene glycol monomethylether and some excess water were distilled off at approximately 95° C. to finally 100° C.

An opaque solution of the target polymer in water having an active level of 54.4% was obtained.

Approximate structure:

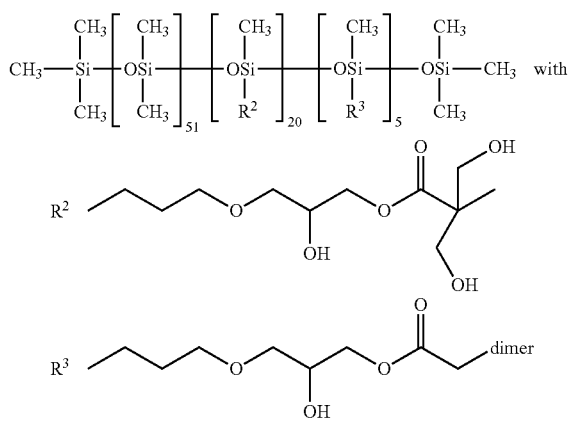

Example 3

One Pot Synthesis of a Copolymer Comprising Pentamer Units and Lactic Acid Moieties

Example 3 (a)

40 g (0.3 mol) of dimethyl propionic acid with 0.06 g (0.0008 mol) of conc. sulfuric acid were charged into a 4-neck flask attached with a mechanical stirrer, dean stark trap and nitrogen in- and out-let. This mixture was quickly heated at 145° C. A slow and constant flow of nitrogen (1 ml/sec) was applied to remove the by-product water formed during the reaction.

About 4.3 g (0.24 mol) of water was collected in the dean stark trap and the flask was quickly cooled to below 90° C. NMR confirms that the pentamer was formed.

Example 3 (b)

Immediately, a solution of 1 g (0.01 mol) of triethylamine in 10 g of propylene glycol monomethylether was charged via an addition funnel. The reaction mixture was stirred for 15 minutes at 80° C.

After that, a solution of 19.2 g (0.0024 mol) of an epoxy silicone of the structure

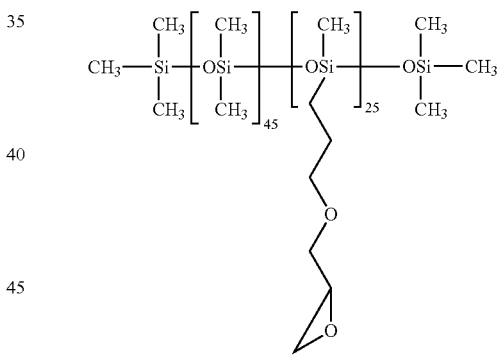

in 95 g of propylene glycol monomethylether was slowly charged via addition funnel. Temperature was further raised after completion of this addition and the reaction mixture was stirred for 18 h at 120° C.

Subsequently, a mixture of 0.1 g of lactic acid, 0.5 of triethylamine and 1 ml of isopropanol in 10 ml of water was added to the reaction mixture and reaction was further continued at 100° C. for 3 h.

After completion of reaction about 30 g of a mixture of water and isopropanol (1:1 by weight) was added to the flask at 100° C. 80 g of solvent mixture were collected at dean Stark trap within 2 h. After this, the reaction mixture was kept under vacuum (8 torr) at 100° C. for ~1.5 h to remove the volatiles. A light brown highly viscous polymer (99.52% solids) was obtained. A NMR analysis showed 100% epoxy group conversion.

Approximate structure:

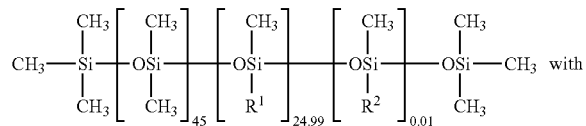

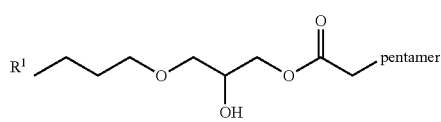

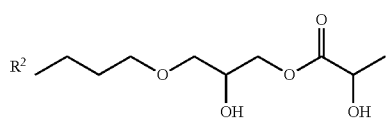

Example 4

One Pot Synthesis of a Copolymer Comprising Pentamer Units, Lauric Acid Moieties and Lactic Acid Moieties Example 4 (a)

26.826 g (0.2 mol) of dimethyl propionic acid with 0.04 g (0.0005 mol) of conc. sulfuric acid were charged into a 4-neck flask attached with a mechanical stirrer, dean stark trap and nitrogen in- and out-let. This mixture was quickly heated at 145° C. A slow and constant flow of nitrogen (1 ml/sec) was applied to remove the by-product water formed during the reaction. About 2.88 g (0.16 mol) of water was collected in dean stark trap and the flask was quickly cooled to below 90° C.

NMR confirms that the pentamer was formed.

Example 4(b)

Immediately, a solution of 1 g (0.01 mol) of triethylamine in 20 g of propylene glycol monomethylether was charged via addition funnel. The reaction mixture was stirred for 10 minutes at 80° C.

After that, a solution of 26 (0.0033 mol) of an epoxy silicone of the structure

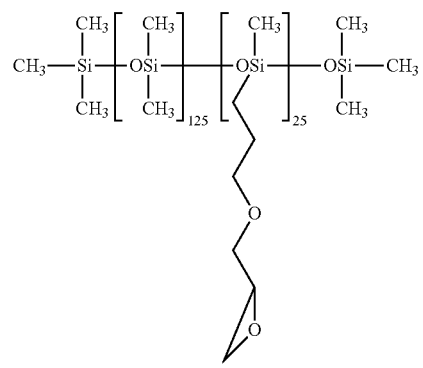

and 2 g (0.0167 mol) of lauric acid in 100 g of propylene glycol monomethylether were slowly charged via an addition funnel. The temperature was further raised after completion of this addition and the reaction mixture was stirred for 18 h at 120° C.

Subsequently, a mixture of 0.1 g of lactic acid and 0.5 g of triethylamine in 10 ml of water-isopropanol mix (1:1 by weight) was added to the reaction mixture and reaction was further continued at 115° C. for 3 h.

After completion of reaction about 40 g of a mixture of water and isopropanol (1:1) was added to the flask at 110° C. 80 g of solvent mixture were collected at dean Stark trap within 2 h. After this, the reaction mixture was kept under vacuum (8 torr) at 100° C. for ~1.5 h to remove the volatiles. A light brown highly viscous polymer (99%/o solids) was obtained. A NMR analysis showed 100% epoxy group conversion.

Approximate structure:

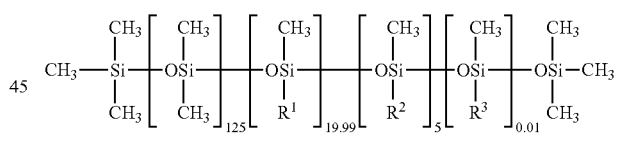

with

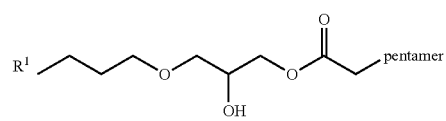

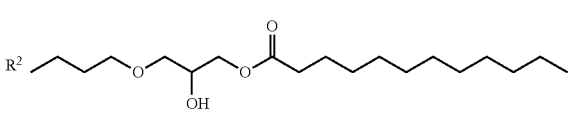

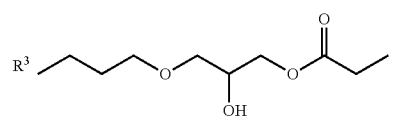

Example 5

Formulation of Microemulsions

A quaternized copolymer of the structure

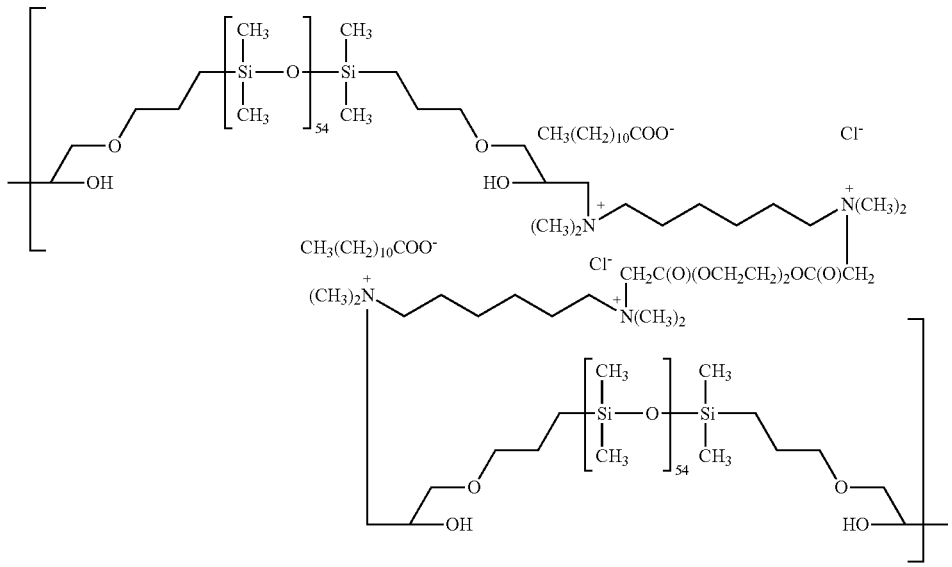

was synthesized according to U.S. Pat. No. 7,217,777, example 11.

2 g of this neat quaternized polymer were mixed with 1 g of different silicones described in the above examples and afterwards slowly mixed with 7 g of distilled water. Target was a 20% active stable and transparent microemulsion of the quaternized silicone.

The following table summarizes the results of the formulation experiments.

| material from example | Inventive yes/no | microemulsion appearance |
|---|---|---|
| 4 | no/monohydroxy | phase separation |
| 5 | no/dihydroxy | strongly turbid |
| 6 | yes/dendrimer | almost transparent |
| 8 | yes/dendrimer | transparent |

The formulation experiments show that monohydroxy acids (example 4) as well as dihydroxy acids (example 5) are not powerful enough with respect to the formation of a hydrophilic silicone based O/W emulsifier. Dendrimer like, polyhydroxylated structures (examples 6 and 8) makes these strongly hydrophilic silicone based O/W emulsifiers accessible.

Example 6

Production of a Copolymer Comprising 2,2-bis-(hydroxymethyl) propionic Acid Ester Units and Oligomer Based Ester Units 26.4 g (0.20 mol) 2,2-bis-(hydroxymethyl) propionic acid, 6.6 g deionized water and 0.15 g sulfuric acid were mixed in a closed glass bottle. The mixture is heated to 110° C. for 8 hours. The degree on oligomerization is 1.87 (1H-NMR analysis).

33 g (0.11 mol —COOH groups) of the oligomer 1.87 solution, 47.06 g (0.35 mol) 2,2-bis-(hydroxymethyl) propionic acid, 219.76 g (0.438 mol epoxy groups) of an epoxide of the structure

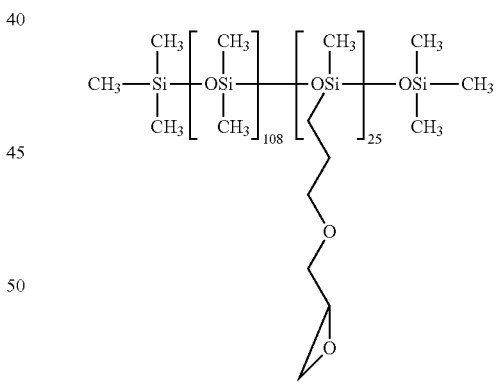

and 3.2 g triethylamine were dissolved in 672.08 g propylene glycol monomethylether.

The mixture was heated to 120° C. for 26 hours. The epoxide conversion was determined by means of NMR (92.7%).

Afterwards, 1344 g water were added stepwise. The azeotrope water/propylene glycol monomethylether and some excess water were distilled off at approx. 95° C. to finally 100° C.

An high viscous, opaque polymer/water dispersion having an active level of 93% is obtained.

Approximate structure:

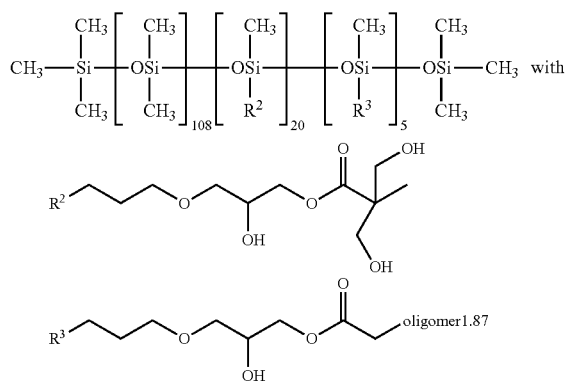 with

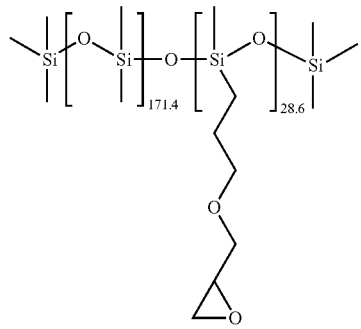

Example 7

19.37 g (0.144 mol) of the 2,2-bis-(hydroxymethyl) propionic acid, 90.17 g (0.144 mol epoxy groups) of a pendant epoxy silicone (D=171.4, $D_{epoxy}$=28.6)

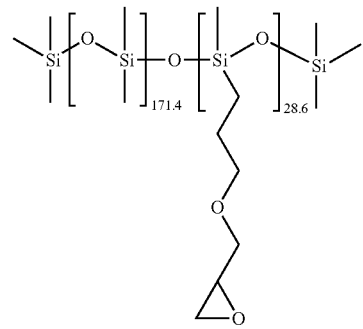

and 1.64 g of triethylamine were dissolved in 109.5 g of dipropylene glycol were charged into a 4-neck flask attached with a mechanical stirrer, condenser, and nitrogen inlet. The mixture was heated to 116° C. for 20 hours. The epoxide conversion was determined by means of titration (>99%).

A viscous, yellow colored polymer solution having an active level of ~50% is obtained.
Approximate structure:

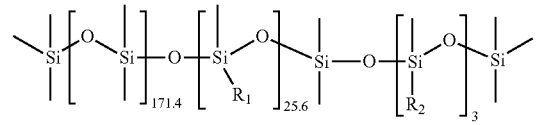

R1 =

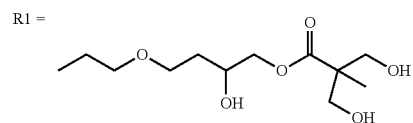

Example 8

17.12 g (0.127 mol) of the 2,2-bis-(hydroxymethyl) propionic acid, 3.68 g (0.018 mol) of lauric acid, 91.14 g (0.144 mol epoxy groups) of a pendant epoxy silicone (D=171.4, $D_{epoxy}$=28.6).

and 1.66 g of triethylamine were dissolved in 110.7 g of dipropylene glycol were charged into a 4-neck flask attached with a mechanical stirrer, condenser, and nitrogen inlet. The mixture was heated to 116° C. for 20 hours. The epoxide conversion was determined by means of titration (>99%).

A viscous, yellow colored polymer solution having an active level of ~50% is obtained.

Approximate structure:

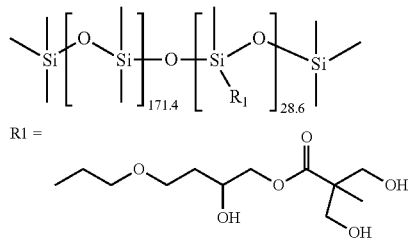

R1 =

R2 =

Example 9

150 g (1.12 mol) 2,2-bis-(hydroxymethyl) propionic acid, 50 g deionized water and 0.6 g conc. sulfuric acid were mixed into a 4-neck flask attached with a mechanical stirrer, dean stark trap and nitrogen inlet. The mixture is heated to 104° C. for 20 hours.

The degree on oligomerization is 3 (titration).

20.95 g (0.057 mol —COOH groups) of the oligomer 3 solution, 35.71 g (0.057 mol epoxy groups) of a pendant epoxy silicone (D=171.4, $D_{epoxy}$=28.6)

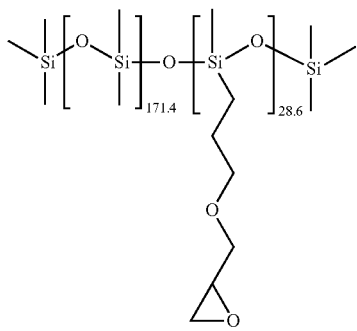

and 0.85 g of triethylamine were dissolved in 56.66 g of dipropylene glycol were charged into a 4-neck flask attached with a mechanical stirrer, condenser, and nitrogen inlet. The mixture was heated to 116° C. for 20 hours. The epoxide conversion was determined by means of titration (>99%).

A viscous, yellow colored polymer solution having an active level of ~50% is obtained. Approximate structure:

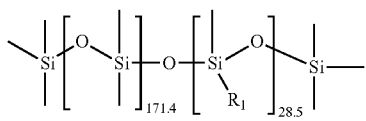

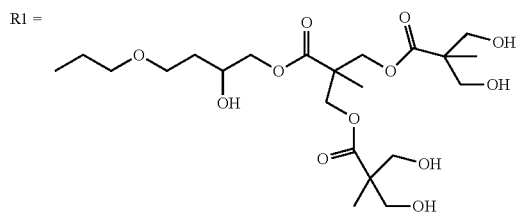

Example 10

20.12 g (0.15 mol) of dimethyl propionic acid with 0.03 g (0.0004 mol) of conc. Sulfuric acid were charged into a 4-neck flask attached with a mechanical stirrer, dean stark trap and nitrogen in- and out-let. This mixture was quickly heated at 140 C. A slow and constant flow of nitrogen (1 ml/sec) was applied to remove the by-product water formed during the reaction. About 1.8 g (0.1 mol) of water was collected in dean stark trap and the flask was quickly cooled to below 90 C.

Immediately, a solution of 0.51 g (0.005 mol) of triethylamine in 10 g of propylene glycol monomethylether was charged via addition funnel. The reaction mixture was stirred for 10 minutes at 80 C.

After that, a solution of 36 g (0.05 mol) of epoxy silicone (D=180, $D_{epoxy}$=25)

in 95 g of propylene glycol monomethylether was slowly charged via addition funnel. Temperature was further raised after completion of this addition and the reaction mixture was stirred for 18 h at 120 C.

Subsequently, a mixture of 0.5 g of lactic acid was added to the reaction mixture and reaction was further continued at 118 C for 2 h.

After completion of reaction about 40 g of a mixture of water and isopropanol (1:1) was added to the flask. The flask was heated initially at 95 C and then at 115 C. 115 g of solvent mixture were collected at dean Stark trap with in 2 h. After this, the reaction mixture was kept under vacuum (8 torr) at 100 C for ~1.5 h to remove the volatiles. A light brown highly viscous polymer (99.5% solids) was obtained. The NMR confirmed the final structure and showed >99% epoxy group conversion.

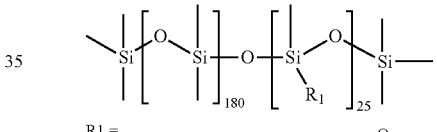

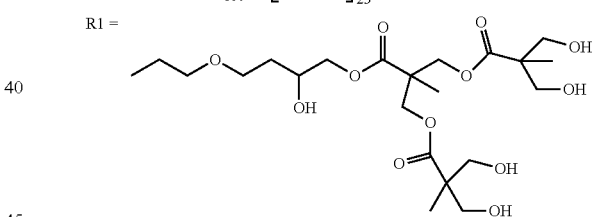

Examples 11 to 14

Antifoam Applications

Testing Method

Crude oil antifoams were tested in the laboratory with a sparging test.

Light crude oil A came from the Southern USA, from a fractured well, with high propensity to foam.

Light crude oil B was a highly paraffinic, light crude with high (about 68° C.) pour point, from a fractured well in the USA.

A 250 mL graduated cylinder was placed in a water bath at the required temperature. The crude sample was preheated and carefully homogenized. Then antifoam solution in 2-ethylhexanol was dosed with a syringe to 50 mL the crude oil sample and nitrogen was bubbled into it at 0.5 L/min flow rate through a 10 micron stainless steel filter. The filter and cylinder were carefully cleaned between the experiments.

The foam height was then monitored. A good antifoam should hold the foam level as low as possible and for as long as possible (durability). Without antifoam, the foam filled up the entire cylinder in about 10 seconds.

Comparative antifoams:

OrgSil1: organomodified siloxane antifoam with high efficiency in oil based foam, made by Momentive Performance Materials.

OrgSil2: organomodified siloxane antifoam with high efficiency in oil based foam, made by Momentive Performance Materials.

Testing Example 11

Table 1 compares the antifoaming efficiency of the two comparative antifoams (at 20 ppm actives) and several of the preparative examples (at 20 and 10 ppm actives). The data show that the preparative examples held the foam at lower level and for much longer time than the comparative examples.

Table 1. Foam height as a function of time with various antifoams, at 20 and 10 ppm actives concentrations, with Light crude oil A, at 40° C.

TABLE 1

Foam height as a function of time with various antifoams, at various ppm doses, With Light crude oil A, at 40° C.

| Antifoam OrgSil2 Time sec | Dose 20 ppm Foam height mL | Antifoam OrgSil2 Time sec | Dose 20 ppm Foam height mL | Antifoam Ex. 7 Time sec | Dose 20 ppm Foam height mL | Antifoam Ex. 9 Time sec | Dose 20 ppm Foam height mL |
|---|---|---|---|---|---|---|---|
| 15 | 120 | 15 | 90 | 15 | 70 | 15 | 70 |
| 45 | 160 | 30 | 100 | 60 | 70 | 60 | 86 |
|  |  | 60 | 110 | 120 | 76 | 120 | 84 |
|  |  | 75 | 130 | 180 | 80 | 240 | 90 |
|  |  | 120 | 150 | 360 | 86 | 360 | 94 |
|  |  | 135 | 160 | 480 | 90 | 420 | 98 |
|  |  |  |  | 540 | 110 | 480 | 110 |
|  |  |  |  | 660 | 130 | 540 | 120 |
|  |  |  |  | 780 | 170 | 660 | 140 |
|  |  |  |  |  |  | 780 | 150 |
|  |  |  |  |  |  | 900 | 160 |

| Antifoam Ex. 10 Time sec | Dose 20 ppm Foam height mL | Antifoam Ex. 10 Time sec | Dose 10 ppm Foam height mL | Antifoam Ex. 8 Time sec | Dose 20 ppm Foam height mL | Antifoam Ex. 8 Time sec | Dose 10 ppm Foam height mL |
|---|---|---|---|---|---|---|---|
| 15 | 64 | 15 | 60 | 15 | 55 | 15 | 60 |
| 60 | 64 | 60 | 66 | 60 | 55 | 60 | 64 |
| 180 | 64 | 120 | 66 | 120 | 60 | 180 | 62 |
| 300 | 62 | 180 | 66 | 180 | 60 | 360 | 62 |
| 360 | 62 | 360 | 66 | 240 | 60 | 540 | 62 |
| 420 | 65 | 420 | 66 | 300 | 65 | 600 | 62 |
| 540 | 66 | 600 | 66 | 360 | 70 | 780 | 64 |
| 660 | 66 | 780 | 68 | 420 | 72 | 900 | 66 |
| 780 | 70 | 960 | 68 | 480 | 80 | 1020 | 74 |
| 840 | 72 | 1080 | 70 | 600 | 70 | 1260 | 100 |
| 900 | 72 | 1320 | 100 | 630 | 80 | 1440 | 135 |
| 960 | 75 | 1500 | 105 | 720 | 84 |  |  |
| 1020 | 78 |  |  | 780 | 80 |  |  |
| 1080 | 82 |  |  | 810 | 70 |  |  |
| 1140 | 92 |  |  | 900 | 80 |  |  |
| 1200 | 96 |  |  | 960 | 86 |  |  |
| 1260 | 102 |  |  | 1020 | 80 |  |  |
| 1320 | 110 |  |  | 1200 | 90 |  |  |
|  |  |  |  | 1260 | 110 |  |  |
|  |  |  |  | 1380 | 130 |  |  |

Testing Example 12

Table 2 shows the antifoaming efficiency of OrgSil1 and Example 6 at various ppm actives with Light crude oil A, at 40° C. The table shows that the Example 6 worked better than the comparative examples even at four time slower dose.

TABLE 2

Foam height as a function of time with various antifoams, at various ppm-actives, with Light crude oil A, at 40° C.

| Antifoam OrgSil1 Time sec | Dose 10 ppm Foam height mL | Antifoam Example 6 Time sec | Dose 10 ppm Foam height mL | Antifoam Example 6 Time sec | Dose 10 ppm Foam height mL | Antifoam Example 6 Time sec | Dose 5 ppm Foam height mL | Antifoam Example 6 Time sec | Dose 2.5 ppm Foam height mL |
|---|---|---|---|---|---|---|---|---|---|
| 15 | 64 | 15 | 62 | 15 | 62 | 15 | 64 | 15 | 69 |
| 60 | 67 | 60 | 60 | 60 | 60 | 60 | 63 | 60 | 69 |
| 120 | 71 | 120 | 59 | 150 | 60 | 120 | 61 | 270 | 69 |
| 180 | 84 | 330 | 58 | 300 | 58 | 300 | 61 | 600 | 70 |
| 240 | 98 | 540 | 56 | 480 | 58 | 480 | 61 | 840 | 70 |
| 300 | 105 | 780 | 56 | 630 | 57 | 600 | 61 | 1200 | 85 |
| 360 | 115 | 1140 | 57 | 960 | 56 | 900 | 63 | | |
| 420 | 123 | | | 1080 | 56 | 1260 | 66 | | |
| 480 | 126 | | | | | 1500 | 70 | | |
| 600 | 144 | | | | | | | | |

Testing Example 13

Table 3 shows the antifoaming efficiency of comparative and preparative examples, with Light crude oil B, at 82° C. The table shows that Example 10 and Example 6 showed competitive performance with the comparative examples.

TABLE 3

Foam height as a function of time with various antifoams, with Light crude oil A, at 40° C.

| Antifoam OrgSil1 Time sec | Dose 20 ppm Foam height mL | Antifoam OrgSil2 Time sec | Dose 20 ppm Foam height mL | Antifoam Example 10 Time sec | Dose 20 ppm Foam height mL | Antifoam Example 6 Time sec | Dose 20 ppm Foam height mL | Antifoam Example 6 Time sec | Dose 20 ppm Foam height mL |
|---|---|---|---|---|---|---|---|---|---|
| 15 | 61 | 15 | 59 | 15 | 61 | 15 | 62 | 15 | 64 |
| 60 | 60 | 60 | 59 | 60 | 63 | 90 | 63 | 60 | 63 |
| 150 | 60 | 120 | 60 | 120 | 72 | 180 | 64 | 120 | 64 |
| 240 | 60 | 180 | 65 | 180 | 103 | 240 | 67 | 240 | 70 |
| 360 | 62 | 240 | 78 | 240 | 147 | 300 | 73 | 300 | 78 |
| 420 | 63 | 300 | 96 | 300 | 190 | 360 | 88 | 360 | 109 |
| 510 | 79 | 360 | 120 | | | 420 | 110 | 420 | 146 |
| 540 | 87 | 420 | 150 | | | 480 | 140 | | |
| 600 | 104 | | | | | 540 | 180 | | |
| 660 | 120 | | | | | | | | |
| 720 | 137 | | | | | | | | |
| 780 | 157 | | | | | | | | |
| 840 | 174 | | | | | | | | |

Example 14

Emulsion Preventor (Non-Emulsifier) Applications

Comparative Emulsion Preventor Example:
Comp1: A commercial non-emulsifier package, routinely used in drilling and fracturing.

Testing Method

The efficiency of the preparative and comparative examples as emulsion preventor was tested by adding them into an aqueous phase, which was, either a./a model water fracturing fluid, containing 10% w/w salt (7.5% NaCl, 2.5% CaCl$_2$), 0.1% biocide, 0.1% friction reducer and 1 lb/1000 gal sodium persulfate in deionized water or b./a model cross-linked fluid which contained 10% w/w salt (7.5% NaCl, 2.5% CaCl2), 0.1% of biocide, 25 lb/1000 gal of guar gel, 3 gal/1000 gal of borate cross-linker, 4 lb/1000 gal of sodium persulfate breaker in deionized water.

The required amount of preparative or comparative example was added to 50 mL of aqueous phase, as described above and poured into prescription glass bottle, which had marks at 10 ml intervals ("San-Glas Ovals-Flint", made by Owen-Brockway, Ill., USA) and threaded cap. Then 50 mL crude oil was also added into the bottle. First, the bottle with the aqueous and crude oil sample was heated for 25 min in a water bath, at the required temperature. Then the liquids were shaken to form an emulsion of the water and oil phase using either a./an Eberbach, reciprocal shaker (from Eberbach Corp, Ann Arbor, Mich., USA), at 280 rpm, for 1 min or b./a malt mixer (HMD 200, from Hamilton Beach Brands, Inc., USA), speed #2 for 30 sec. The emulsion was then poured into one or two medicine bottles, and kept them in the bath.

The separation of the water phase in the bottle(s) was monitored. The separation time was when all the water phase separated and no emulsion can be observed along the oil/water interface.

Table 4 shows the emulsion preventor (non-emulsifier) efficiency of comparative and preparative examples, with Light crude oil A, at 84° C. The preparation examples showed high performance compared to the comparative example.

TABLE 4

Separation time of emulsions in the presence of various emulsion preventors, using Light crude A, model water fracturing fluid and Eberbach shaker, at 84° C.

| Emulsion Preventor | Dose (ppm) | Separation time (sec) |
|---|---|---|
| None | 0 | 180 |
| W54 available from Schlumberger | 1000 | 50 |
| The material of Example 3 | 150 | 25-30 |
| The material of Example 3 | 500 | 20-25 |
| The material of Example 10 | 150 | 15-20 |
| The material of Example 7 | 150 | 10-15 |
| The material of Example 8 | 150 | 15-20 |
| The material of Example 9 | 150 | 45-50 |
| The material of Example 6 | 150 | 15-20 |

Table 5 shows the emulsion preventor (non-emulsifier) efficiency of comparative and preparative examples, with Light crude oil A, at 84° C. The table illustrates that the preparation examples showed superior performance relative to the comparative example.

TABLE 5

Separation time of emulsions in the presence of various emulsion preventors, using Light crude A, model cross-linked fluid and malt mixer, at 84° C.

| Emulsion Preventor | Dose (ppm) | Separation time (sec) |
|---|---|---|
| None | 0 | 240 |
| W54 available from Schlumberger | 1000 | 50 |
| The material of Example 3 | 150 | 35 |

What is claimed is:

1. A polysiloxane compound having the general formula (I):

$$[M_a D_b D^*_c T_d Q_e]_f \quad (I)$$

wherein
$M = R^1 R^2 R^3 SiO_{1/2}$;
$D = R^4 R^5 SiO_{2/2}$;
$D^* = R^6 R^7 SiO_{2/2}$;
$T = R^8 SiO_{3/2}$;
$Q = SiO_{4/2}$;
with
$a = 1-10$
$b = 0-1000$
$c = 0-1000$
$d = 0-1$
$e = 0-1$
$f = 1-10$
wherein
$R^1$, $R^2$, $R^3$, $R^4$, $R^5$, $R^6$ and $R^8$ are each independently selected from the group consisting of monovalent hydrocarbon groups having from 1 to 8 carbon atoms, and an aryl or alkaryl hydrocarbon group of from 6 to 22 carbon atoms, or $R^7$;
$R^7$ is selected from the group consisting of $R^9$, $R^{10}$ and $R^{11}$,
wherein
$R^9$ is selected from the group consisting of —Z-(A-$E^1$)$_y$, —Z-$E^2$ and —Z—NH—C(O)—$R^{12}$, wherein
Z is a bivalent or trivalent straight-chained, cyclic or branched, saturated or unsaturated $C_2$ to $C_{20}$ hydrocarbon residue which can comprise one or more groups selected from —O—, —NH—,

and can be substituted by one or more OH groups,
A is a bivalent residue selected from the group consisting of

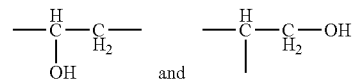

and $E^1$ is selected from the group consisting of $E^2$ and $E^3$
wherein $E^2 = $ —O—C(O)—$R^{12}$, wherein

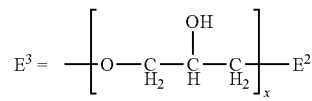

wherein $E^2$ is defined above, and $x = 1-4$, $y = 1$ or 2
$R^{10}$ is selected from the group consisting of —Z-(A-$E^4$)$_{y'}$, —Z-$E^5$ and —Z—NH—C(O)—$R^{13}$,
wherein
Z and A are defined above,
$E^4$ is selected from the group consisting of $E^5$ and $E^6$
wherein $E^5 = $ —O—C(O)—$R^{13}$, wherein
$R^{13}$ is a straight-chained, cyclic or branched, saturated or unsaturated hydrocarbon residue with up to 9 carbon atoms, which can comprise one or more groups selected from —O—, —NH—, —$NR^{14}$—, —C(O)—, and is substituted by one or more OH groups, wherein $R^{14}$ is a straight-chained, cyclic or branched, saturated or unsaturated hydrocarbon residue with up to 6 carbon atoms,

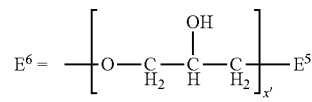

wherein $E^5$ is defined above, and $x' = 1-4$, $y' = 1$ or 2
$R^{11}$ is selected from the group consisting of —Z-(A-$E^7$)$_{y'}$, —Z-$E^8$ and —Z—NH—C(O)—$R^{15}$,
wherein
Z and A are defined above,
$E^7$ is selected from the group consisting of $E^8$ and $E^9$
wherein $E^8 = $ —O—C(O)—$R^{15}$, wherein
R$^{15}$ is a straight-chained, cyclic or branched, saturated or unsaturated hydrocarbon residue with 10 to 50 carbon atoms, which can comprise one or more groups selected from —O—, —NH—, —NR$^{16}$—, —C(O), and is optionally substituted by one or more OH groups, wherein R$^{16}$ is a straight-chained, cyclic or branched, saturated or unsaturated hydrocarbon residue with up to 6 carbon atoms,

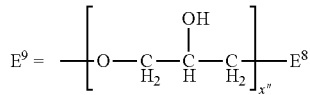

wherein E$^8$ is defined above, and x″=1–4, y″=1 or 2, with the proviso that the polysiloxane compound comprises R$^9$;

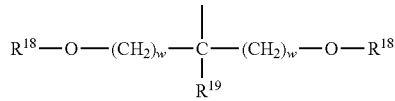

wherein R$^{12}$ is
wherein
R$^{19}$=R$^{17}$ or H,
R$^{17}$ is C$_1$ to C$_{22}$-alkyl, fluoro-substituted C$_1$ to C$_{22}$-alkyl or aryl,
w=1–3,
R$^{18}$=H or

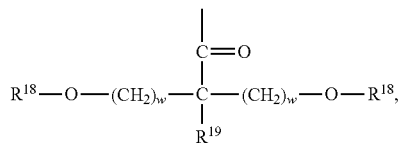

provide that the total number of carbon atoms in R$^{12}$ is 5 to 70 and at least one ester bond is present in R$^{12}$.

2. The polysiloxane compound according to claim 1, comprising structural elements selected from the following structures:

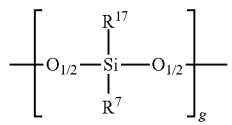

wherein R$^{17}$ is C$_1$ to C$_{22}$-alkyl, fluoro-substituted C$_1$ to C$_{22}$-alkyl or aryl, and
g=0–600,

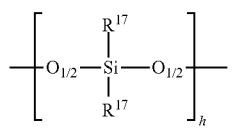

wherein the groups R$^{17}$ can be the same or different and are selected from C$_1$ to C$_{22}$-alkyl, fluoro-substituted C$_1$ to C$_{22}$-alkyl and aryl, and
h=0–700,

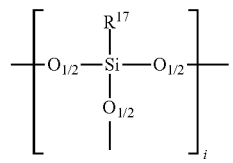

wherein R$^{17}$ is as defined above, and
i=0–10,

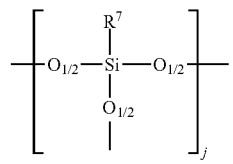

wherein R$^7$ is as defined above, and
j=0–10,

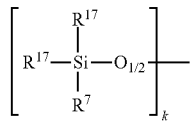

wherein R$^7$ and R$^{17}$ are as defined above, and
k=0–30,

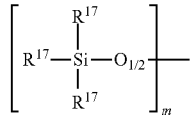

wherein R$^{17}$ is as defined above, and
m=0–30,

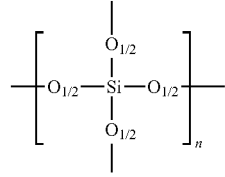

wherein n=0–10,
g+h+i+j+k+m+n=12–1000.

3. The polysiloxane compound according to claim 2, comprising structural elements selected from the following structures:

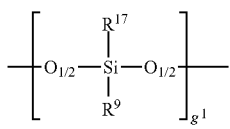

wherein $R^9$ and $R^{17}$ are defined above, and
$g^1=0-300$,

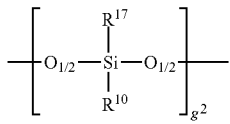

wherein $R^{10}$ and $R^{17}$ are defined above, and
$g^2=0-300$,

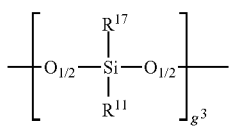

wherein $R^{11}$ and $R^{17}$ are defined above, and
$g^3=0-300$,

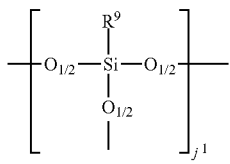

wherein $R^9$ is defined above, and
$j^1=0-10$,

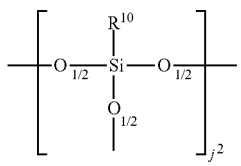

wherein $R^{10}$ is defined above, and
$j^2=0-10$,

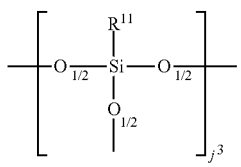

wherein $R^{11}$ is defined above, and
$j^3=0-10$,

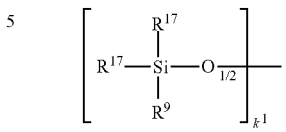

wherein $R^9$ and $R^{17}$ are defined above, and
$k^1=0-15$,

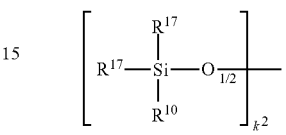

wherein $R^{10}$ and $R^{17}$ are defined above, and
$k^2=0-15$,

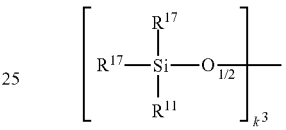

wherein $R^{11}$ and $R^{17}$ are defined above, and
$k^3=0-15$, and
$g^1+g^2+g^3+h+i+j^1+j^2+j^3+k^1+k^2+k^3+m+n=12$ to 1000.

4. The polysiloxane compound according to claim 2, wherein $R^{17}$ is methyl or $h=3-500$ or $i=0$ or $m=1-6$ or $n=0$.

5. The polysiloxane compound according to claim 3, wherein $R^{17}$ is methyl or $g^1=2-200$ or $g^2=0-200$ or $g^3=0-200$ or $j^1=0$ or $j^2=0$ or $j^3=0$ or $k^1=0-2$ or $k^2=0-2$ or $k^3=0-2$ or $g^1+g^2+g^3+h+i+j^1+j^2+j^3+k^1+k^2+k^3+m+n=15$ to 400 or $h+k^1=2-1000$.

6. The polysiloxane compound according to claim 1, wherein the molar ratio of $R^9$ to $R^{17}$ is 10:1 to 1:10.

7. The polysiloxane compound according to claim 1, wherein the polysiloxane compound either do not contain hydrophilic residues $R^{10}$ and/or lipophilic residues $R^{11}$ or the molar ratio of the siloxy units comprising the dendrimer residue $R^9$ to the siloxy units comprising hydrophilic residues $R^{10}$ and lipophilic residues $R^{11}$ in the polysiloxane compound is 1:0.01 to 1:100.

8. The polysiloxane compound according to claim 1, wherein the molar ratio of $R^9$ to $R^{10}$ and $R^{11}$ is 1:0.1 to 1:10.

9. The polysiloxane compound according to claim 1, wherein $R^{17}$ is $C_1$ to $C_{10}$-alkyl, optionally substituted with 1 to 13 fluoro atoms, and aryl.

10. The polysiloxane compound according to claim 1, wherein Z is a bivalent or trivalent straight-chained, cyclic or branched, saturated or unsaturated $C_2$ to $C_{10}$ hydrocarbon residue, which can comprise —O— groups and can be substituted by one or more OH groups.

11. The polysiloxane compound according to claim 1, wherein Z is a bivalent or trivalent straight-chained, cyclic or branched, saturated or unsaturated $C_2$ to $C_6$ hydrocarbon residue which can comprise one or more groups selected from —O—, —NH—,

and can be substituted by one or more OH groups.

12. The polysiloxane compound according to claim 1, wherein y=1 or x=1.

13. The polysiloxane compound according to claim 1 wherein $R^{19}$ is $CH_3$, and w=1.

14. The polysiloxane compound according to claim 1 wherein the number of ester bonds present in $R^{12}$ is 1 to 14.

15. The polysiloxane compound according to claim 1 wherein

Z=—$CH_2CH_2CH_2$—O—$CH_2$—,

—$CH_2CH_2CH_2CH_2$—,

—CH=$CH_2CH_2$—,

—CH=$CH_2CH_2CH_2$—,

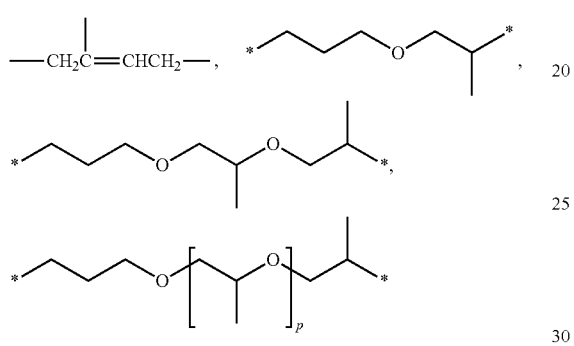

p=1 to 4,

* marks a bond to the silicon atom in each case.

16. The polysiloxane compound according to claim 1 wherein —Z-A- is selected from the cyclic structures which are derived from cyclic epoxides.

17. The polysiloxane compound according to claim 1 wherein cyclic epoxides are selected from the group consisting of

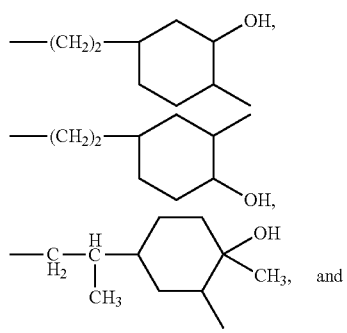

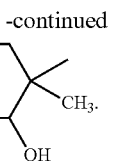

18. A cosmetic formulation comprising the polysiloxane compound according to claim 1 and at least one cosmetic ingredient.

19. The polysiloxane compound of claim 1 wherein $R^{12}$ is selected from the group consisting of

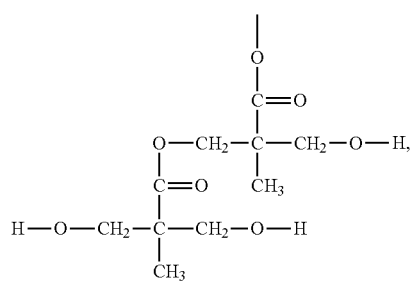

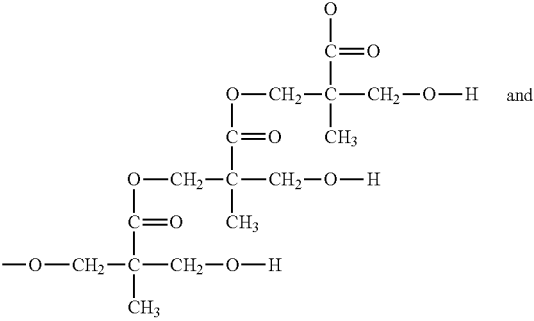

and

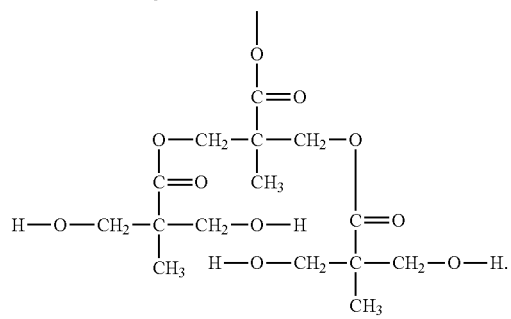

* * * * *